United States Patent
Jacobs

(10) Patent No.: US 8,657,763 B2
(45) Date of Patent: Feb. 25, 2014

(54) VACUUM ASSISTED LANCING SYSTEM WITH ELECTIVE VACUUM RELEASE AND METHOD FOR BLOOD EXTRACTION WITH MINIMAL PAIN

(76) Inventor: Christopher A. Jacobs, Midland, TX (US)

( * ) Notice: Subject to any disclaimer, the term of this patent is extended or adjusted under 35 U.S.C. 154(b) by 0 days.

(21) Appl. No.: 13/367,953

(22) Filed: Feb. 7, 2012

(65) Prior Publication Data

US 2012/0143086 A1    Jun. 7, 2012

Related U.S. Application Data

(63) Continuation-in-part of application No. 12/689,570, filed on Jan. 19, 2010, now Pat. No. 8,480,596, which is a continuation-in-part of application No. 12/689,608, filed on Jan. 19, 2010, now Pat. No. 8,460,210, which is a continuation-in-part of application No. 12/689,618, filed on Jan. 19, 2010, now Pat. No. 8,485,990, which is a continuation-in-part of application No. 12/689,641, filed on Jan. 19, 2010, now Pat. No. 8,460,211, which is a continuation-in-part of application No. 12/689,657, filed on Jan. 19, 2010, now Pat. No. 8,485,991.

(51) Int. Cl.
*A61B 5/00* (2006.01)
*B65D 81/00* (2006.01)

(52) U.S. Cl.
USPC ........... 600/583; 600/573; 600/576; 600/578; 600/579; 606/172; 606/181; 606/182

(58) Field of Classification Search
USPC .......... 600/573, 576, 578, 579, 583; 606/181, 606/182
See application file for complete search history.

(56) References Cited

U.S. PATENT DOCUMENTS

| 4,653,513 A | 3/1987 | Dombrowski |
| 5,320,607 A | 6/1994 | Ishibashi |

(Continued)

FOREIGN PATENT DOCUMENTS

| EP | 1 219 242 | 7/2002 |
| EP | 1 449 479 | 8/2004 |

(Continued)

OTHER PUBLICATIONS

Schultz, O., International Search Report for International Patent Application No. PCT/US2011/020104, dated Dec. 19, 2011, European Patent Office.

(Continued)

*Primary Examiner* — Jeffrey G Hoekstra
*Assistant Examiner* — Devin Henson
(74) *Attorney, Agent, or Firm* — Locke Lord LLP

(57) ABSTRACT

A vacuum assisted lancing system for blood extraction can include a tubular body having a vacuum chamber, a lancing mechanism configured to removably couple with a lance, a vacuum mechanism including a piston slideably coupled within the body, a release mechanism for selectively holding the vacuum mechanism in an energized state, and an opening for allowing fluid communication between the vacuum chamber and an atmosphere surrounding the vacuum chamber. The system can include structure for selectively commencing dissipation of the vacuum and a fixed or adjustable depth controller. A method of manipulating a surface for blood extraction can include coupling the lancing system to the surface, blocking the opening, creating a vacuum, moving the lance coupler from a first position distal from the surface to a second position proximal to the surface, maintaining the vacuum for a period of time, and commencing dissipation of the vacuum by unblocking the opening.

20 Claims, 25 Drawing Sheets

(56) References Cited

U.S. PATENT DOCUMENTS

| | | | |
|---|---|---|---|
| 5,666,966 | A | 9/1997 | Horie et al. |
| 5,873,887 | A * | 2/1999 | King et al. ............... 606/182 |
| 6,026,841 | A | 2/2000 | Kozik |
| 6,027,459 | A | 2/2000 | Shain et al. |
| 6,063,039 | A | 5/2000 | Cunningham et al. |
| 6,071,249 | A | 6/2000 | Cunningham et al. |
| 6,071,251 | A | 6/2000 | Cunningham et al. |
| 6,093,156 | A | 7/2000 | Cunningham et al. |
| 6,152,942 | A | 11/2000 | Brenneman et al. |
| 6,155,992 | A | 12/2000 | Henning et al. |
| 6,206,841 | B1 | 3/2001 | Cunningham et al. |
| 6,261,245 | B1 * | 7/2001 | Kawai et al. ............... 600/576 |
| 6,283,926 | B1 | 9/2001 | Cunningham et al. |
| 6,306,104 | B1 | 10/2001 | Cunningham et al. |
| 6,837,858 | B2 | 1/2005 | Cunningham et al. |
| 7,662,111 | B2 * | 2/2010 | Cha et al. ............... 600/583 |
| 2004/0249406 | A1 | 12/2004 | Griffin et al. |
| 2009/0043324 | A1 * | 2/2009 | Paschal ............... 606/181 |

FOREIGN PATENT DOCUMENTS

| | | |
|---|---|---|
| JP | 11 206742 | 8/1999 |
| WO | 2005/013823 | 2/2005 |

OTHER PUBLICATIONS

Schultz, O., Written Opinion for International Patent Application No. PCT/US2011/020104, dated Dec. 19, 2011, European Patent Office.

* cited by examiner

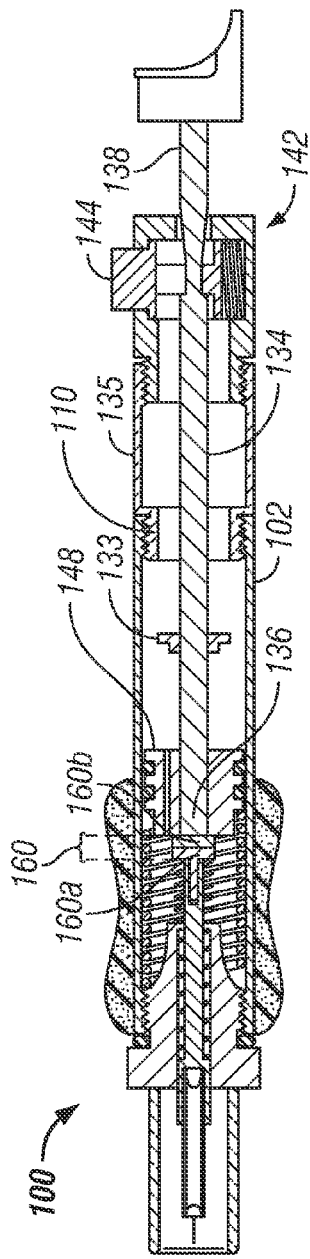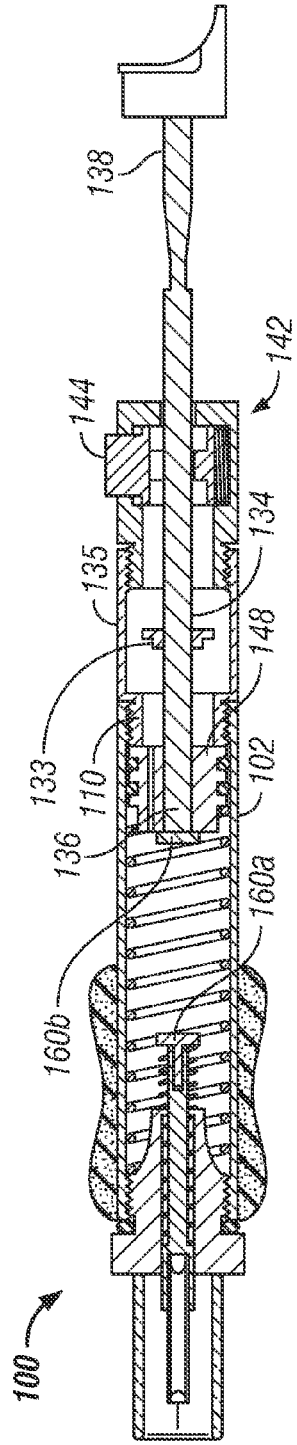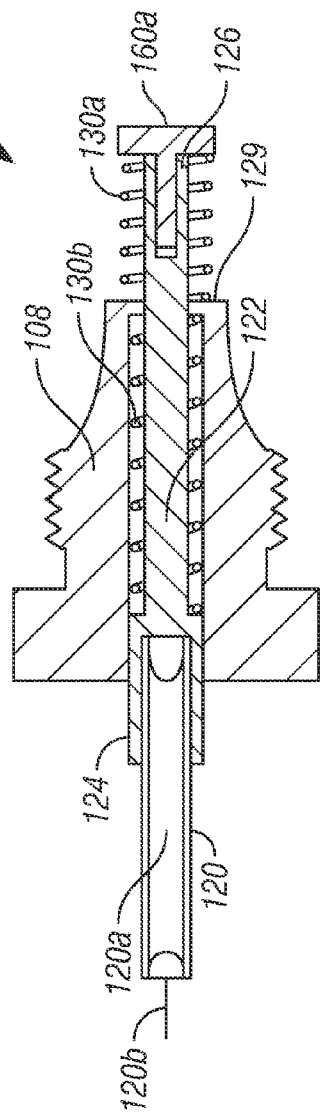

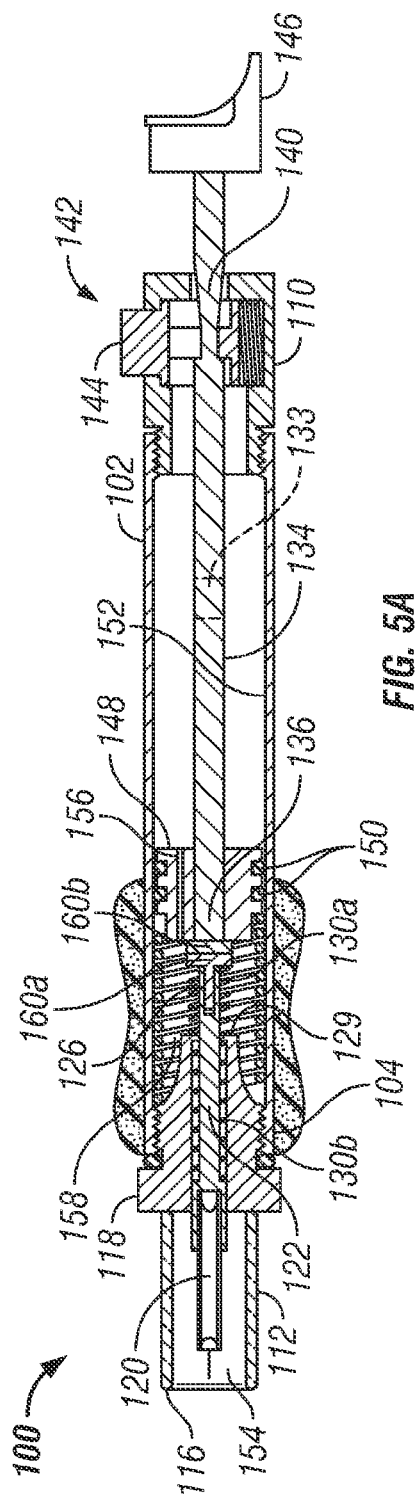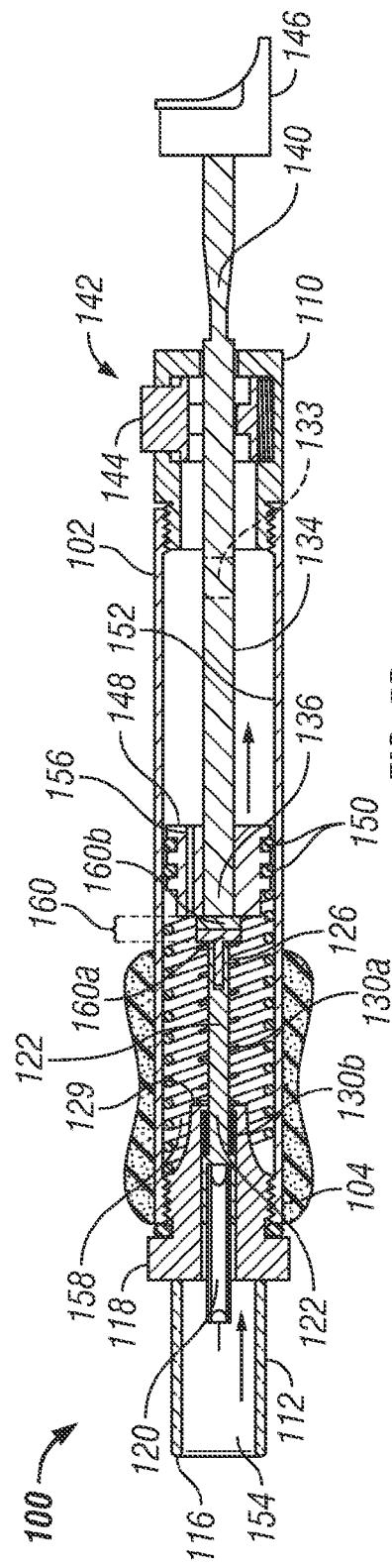
FIG. 5A
FIG. 5B

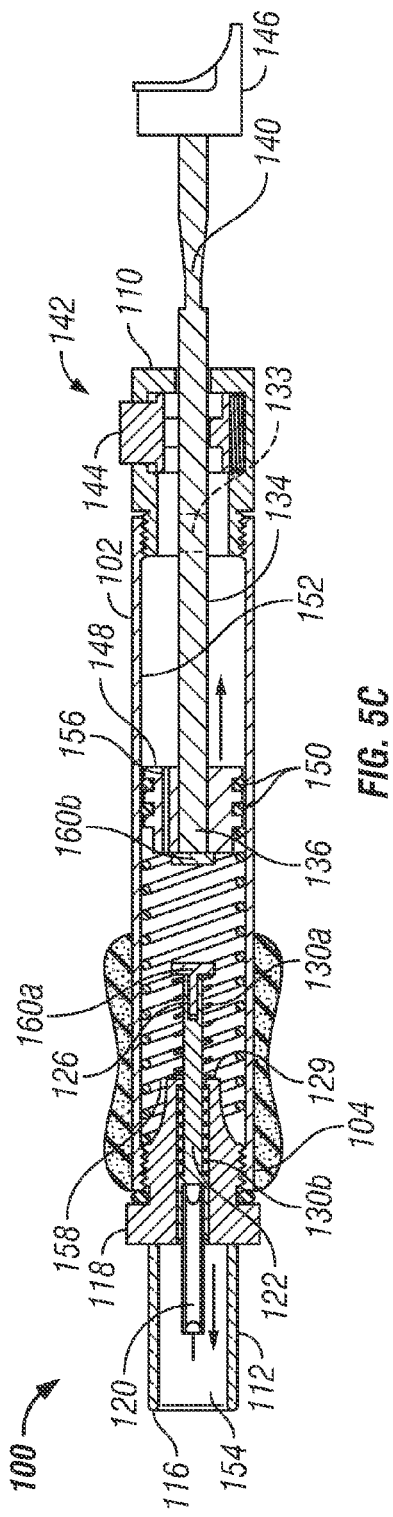
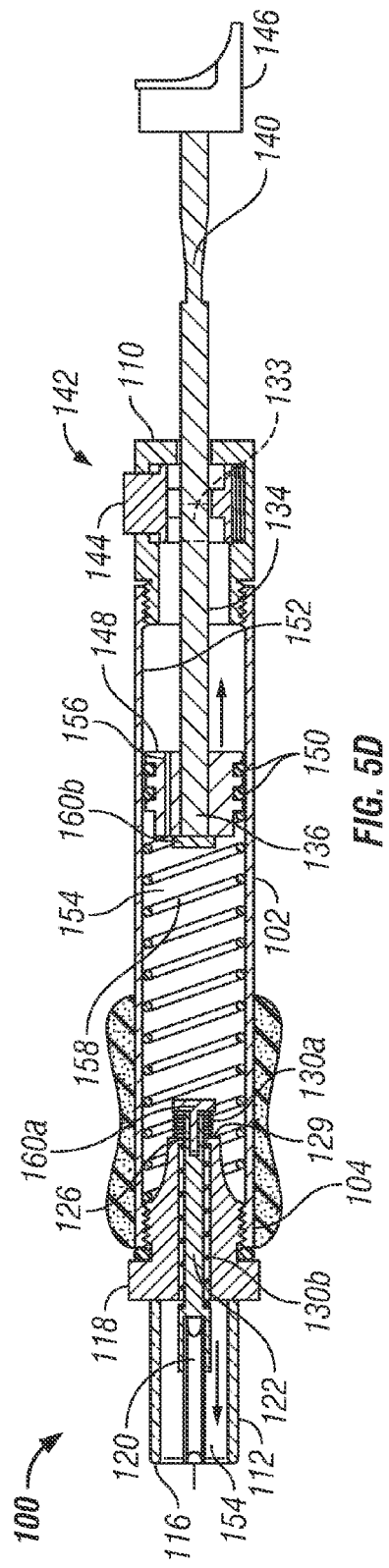
FIG. 5C
FIG. 5D

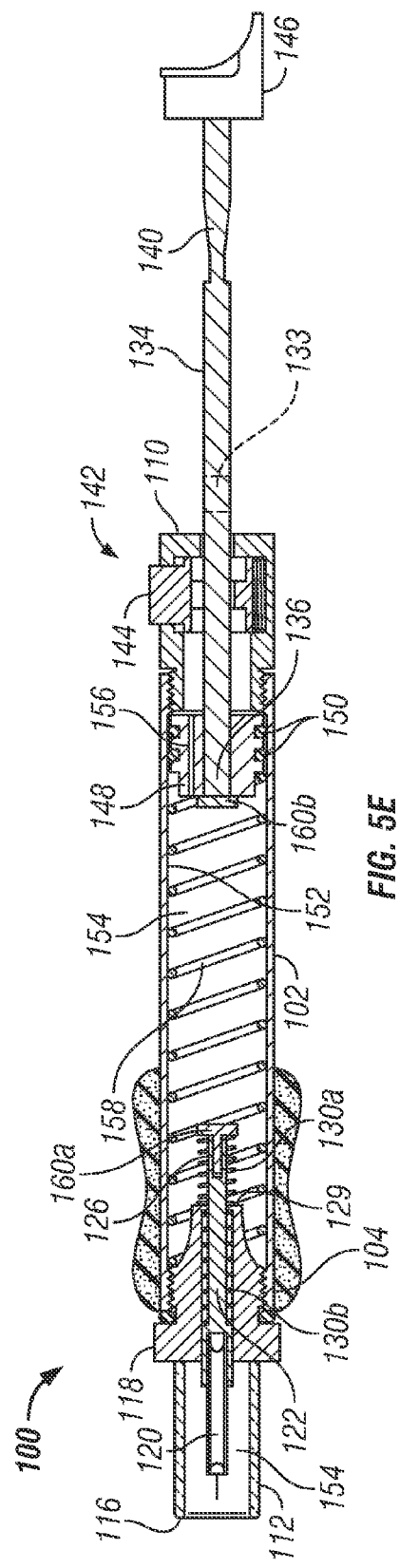
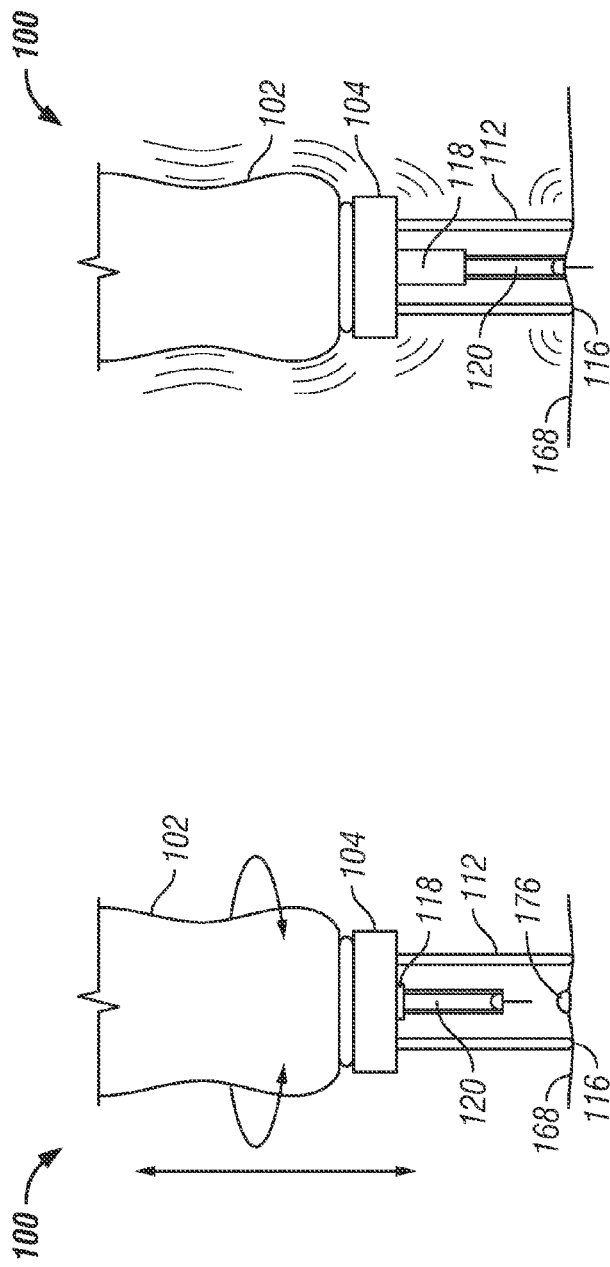
FIG. 5E
FIG. 5F
FIG. 5G

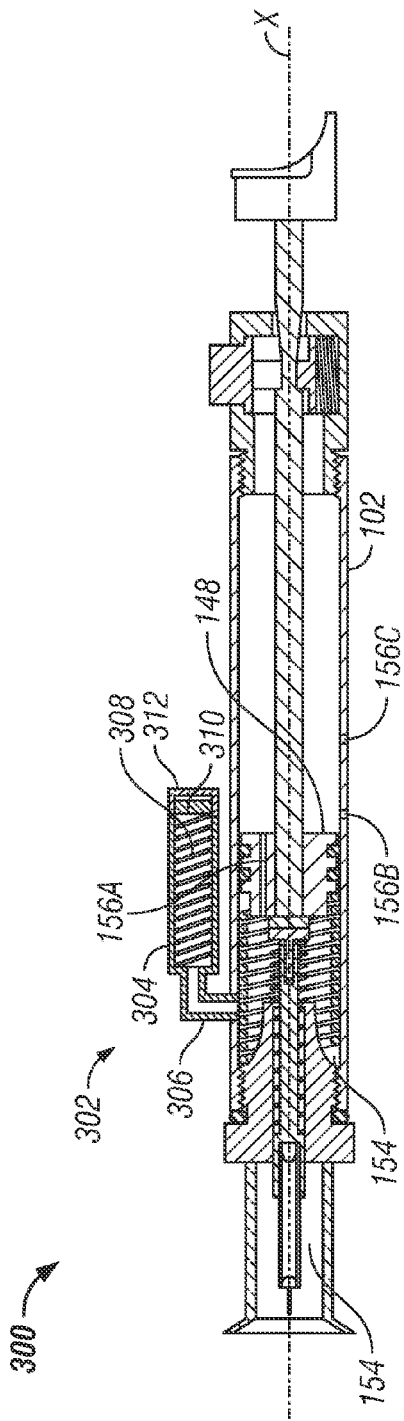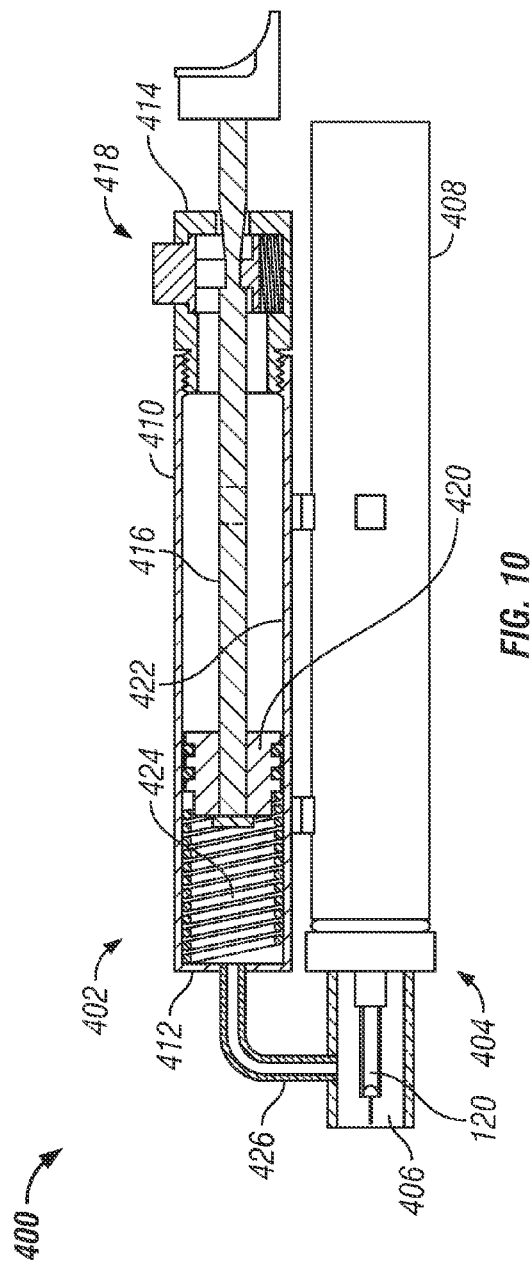

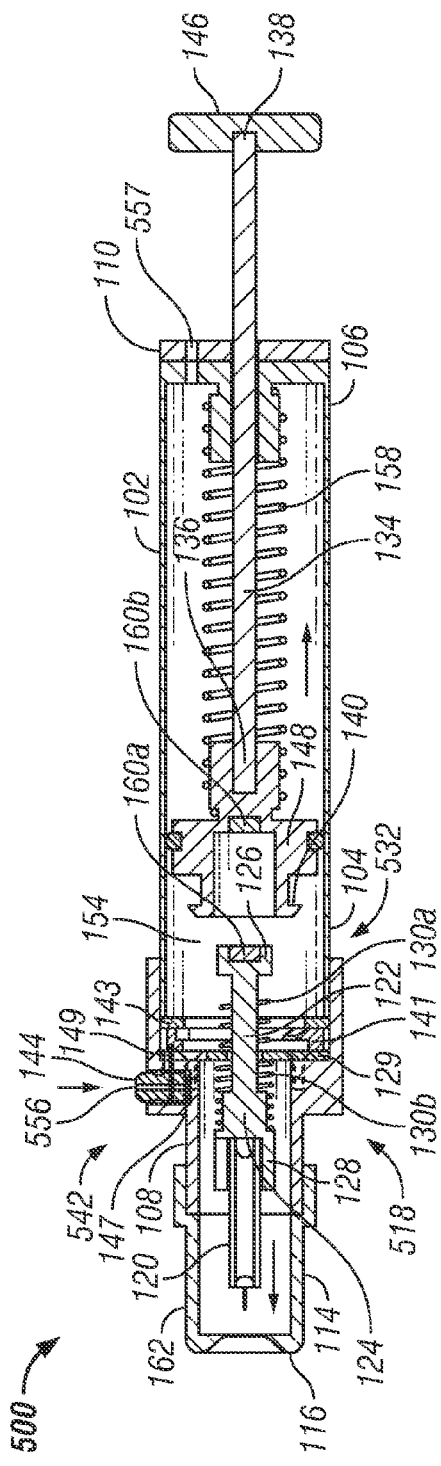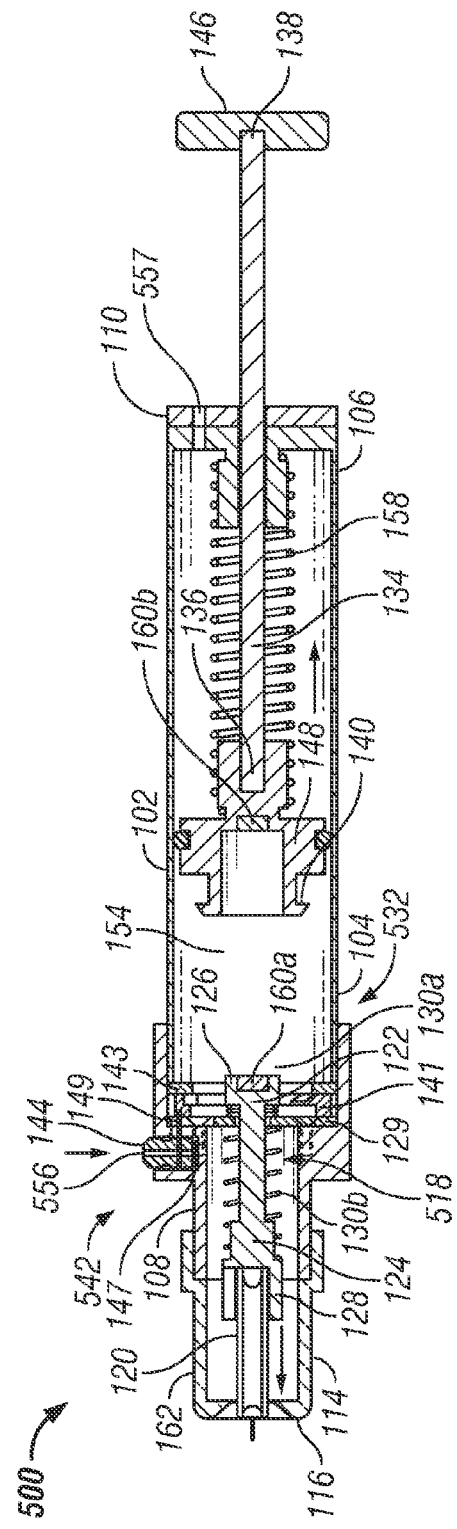

VACUUM ASSISTED LANCING SYSTEM WITH ELECTIVE VACUUM RELEASE AND METHOD FOR BLOOD EXTRACTION WITH MINIMAL PAIN

CROSS REFERENCE TO RELATED APPLICATIONS

This application is a continuation-in-part of U.S. Ser. Nos. 12/689,570; 12/689,608; 12/689,618; 12/689,641; and 12/689,657; each of which was filed on Jan. 19, 2010.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

1. Field of the Invention

The invention disclosed and taught herein relates generally to blood extraction devices and methods. More specifically, the invention relates to vacuum assisted lancing devices and methods useful for extracting a quantity of blood for sampling or testing.

2. Description of the Related Art

There are many medical reasons where a small quantity of blood needs to be drawn from a human. Determining blood glucose levels for diagnosis and treatment of diabetes is one of the most common applications where access to blood is required. Diabetes has become a significant health risk in the United States and other parts of the world. The rise in diabetes has caused alarm in the medical community. Major companies, research institutions, and the consuming public are collectively spending significant resources for the prevention, testing, and treatment of diabetes. A person with diabetes is generally required to test their blood several times a day for glucose levels and take corrective action if needed. Failure to test and take corrective action when necessary can result in injury, both long and short term degradation of the human body's functions, and in some cases death.

Currently, the market provides an assortment of devices that lance the skin producing a wound or other opening from which blood can be extracted. However, most require testing on an area of a user's skin that has a high concentration of blood vessels near the surface of the skin so that the lance can produce an acceptable quantity of blood. The most common area for testing is the finger tips, although the toes have also been used. However, these heavily vasculated areas of the human body are typically highly sensitive, having a rich supply of nerve endings. As a result, blood rich areas, such as the finger tips, often are more pain sensitive than other less vasculated areas. Thus, the very areas that are ideally suited for extracting blood for testing are the most sensitive to pain.

For those individuals who are required to test themselves, the frequent testing can have negative effects on their emotional health, physical health, and even personalities. At the least, in an effort to avoid pain, they are motivated to not test as often as required by their physician. A loss of frequency and continuity in the testing can lead to physical and emotional complications, or a significant loss of accuracy in determining proper dietary corrections and medicine regiments. Health care practitioners may also be required to lance a patient's skin to extract blood for testing, which is typically done in the fingers. In some situations, however, the fingers and toes may not be available for testing, such as when these areas of the patient's body are bandaged or injured, and an alternative testing site on the patient's body may be required.

Some blood extraction devices simply lance the skin and the patient manually squeezes the area to produce the required quantity of blood. Other blood extraction devices seek to use a vacuum to enhance the blood recovery from the lancing. However, in surveying the market of such devices, the inventor has realized that the vacuum assisted devices are either not portable with mechanized vacuum pumps, which can significantly diminish their value for mobile patients, or require unwanted maintenance, such as replacement of batteries, which are not always available. Further, many of such devices fail to adequately produce a desirable quantity of blood from portions of the skin other than the fingers and toes. Newer devices house multiple lances in the same holder, and with each use a new lance is automatically selected and used such that the patient never uses the same lance twice. Many, if not all, of these devices, including the ones that apply a vacuum, have been unsuccessful in reliably extracting sufficient quantities of blood from areas of the skin less painful than the fingers and toes. Reduction or elimination of pain has been shown to appreciably encourage the patient to follow the testing procedure prescribed by an attending physician.

While each of these devices may have certain limited applications, there remains a need to provide a simplified and improved vacuum assisted lancing device that can be routinely used at various places on the skin and still extract a sufficient quantity of blood for the required test.

BRIEF SUMMARY OF THE INVENTION

A vacuum assisted lancing system for blood extraction can include a tubular body having a vacuum chamber, a lancing mechanism configured to removably couple with a lance, a vacuum mechanism including a piston slideably coupled within the body, a release mechanism for selectively holding the vacuum mechanism in an energized state, and an opening for allowing fluid communication between the vacuum chamber and an atmosphere surrounding the vacuum chamber. The system can include means for selectively commencing dissipation of the vacuum. A method of manipulating a surface for blood extraction can include coupling the lancing system to the surface, blocking the opening, creating a vacuum, moving the lance coupler from a first position distal from the surface to a second position proximal to the surface, maintaining the vacuum for a period of time, and commencing dissipation of the vacuum by unblocking the opening.

A vacuum assisted lancing system for blood extraction can include a body having a central longitudinal axis, a lancing end and a free end, a lancing mechanism coupled with the body and adapted to removably couple with a lance, a vacuum mechanism coupled with the body and including a piston slideably coupled with the body so that a vacuum chamber can be formed between the piston and the lancing end of the body, a release mechanism adapted to selectively hold the vacuum mechanism in an energized state, and an opening through the body that can allow fluid communication between the vacuum chamber and an atmosphere surrounding the vacuum chamber. The opening through the body can be adapted to be sealingly engaged by a user so that the user can selectively block and unblock the opening.

The release mechanism can include a release, and the opening can be disposed in the release. The release can have an activated position, and the opening can be adapted to be at least partially blocked when the release is in the activated position. The system can include a valve coupled to the opening, and can include a tubular lance guide removably coupled to the body and adapted to sealingly engage a surface to be lanced. The lance guide can have a transparent viewing area for viewing the surface. The system can include a depth controller coupled to the body and adapted to sealingly engage a surface to be lanced. The depth controller can be fixed or adjustable and can include a spacer having a variable thickness. The system can include a lance coupled to the lancing mechanism.

A vacuum assisted lancing system for blood extraction can include a body having a first end adapted to sealingly engage a surface to be lanced, a longitudinally opposite second end, and a vacuum chamber between the first and second ends, means for creating a vacuum in the vacuum chamber and acting on the surface, means for disposing a lance in contact with the surface while the vacuum is acting on the surface, and means for selectively commencing dissipation of the vacuum after the vacuum has acted on the surface for a period of time. The means for selectively commencing dissipation of the vacuum can include an opening through the body for allowing fluid communication between the vacuum chamber and an atmosphere surrounding the vacuum chamber. The means for creating a vacuum can include a release coupled to the body, and the opening through the body can be disposed through the release. The system can include means for simultaneously initiating creation of the vacuum and at least partially blocking the opening. The system can include means for dissipating the vacuum at a controlled rate. The system can include a lance coupled to the means for disposing a lance in contact with the surface.

A method of manipulating a surface for blood extraction can include coupling a lancing system to the surface, blocking an opening, activating the lancing system, thereby creating a vacuum, subjecting the surface to the vacuum, and moving a lance coupler from a first position distal from the surface to a second position proximal to the surface, maintaining the vacuum for a period of time, and commencing dissipation of the vacuum. Commencing dissipation of the vacuum can include unblocking the opening and allowing the surface to fluidicly communicate with an atmosphere surrounding the lancing system while the lancing system is coupled to the surface.

The lancing system can include a release coupled with the opening, and the blocking and activating steps can be accomplished simultaneously by engaging and holding the release. Commencing dissipation of the vacuum can include disengaging the release. Blocking the opening can include sealingly engaging the opening with a finger or other body, and unblocking the opening can include disengaging the opening and the finger or other body. The lancing system can include a lance removably coupled to a lance coupler, and the method can include lancing the surface. The method can include maintaining the vacuum for a period of time after the surface has been lanced, and can include verifying that an amount of blood has been extracted prior to commencing dissipation of the vacuum.

BRIEF DESCRIPTION OF THE SEVERAL VIEWS OF THE DRAWINGS

FIG. 3A is a cross-sectional schematic view of another of many embodiments of a vacuum lance system having an indicator according to the disclosure.

FIG. 3B is a cross-sectional schematic view of the indicator of FIG. 3A in a viewing window.

FIG. 4 is a cross-sectional schematic view of one of many embodiments of a lancing mechanism according to the disclosure.

FIG. 5A is an illustration of one of many embodiments of a vacuum lance system in a cocked position according to the disclosure.

FIGS. 5B, 5C and 5D are illustrations of the system of FIG. 5A in three respective positions during lancing.

FIG. 5E is an illustration of the system of FIG. 5A in an uncocked position.

FIG. 5F is an illustration of the system of FIG. 5A manipulating a surface during lancing.

FIG. 5G is an illustration of the system of FIG. 5A vibrating a surface during lancing.

FIG. 9 is a cross-sectional schematic view of one of many embodiments of a vacuum lance system having an external vacuum indicator according to the disclosure.

FIG. 10 is a cross-sectional schematic view of one of many embodiments of a vacuum lance system having an external vacuum assembly according to the disclosure.

FIG. 15C is an illustration of the vacuum lance system of FIG. 15A in another of many activated positions wherein the first and second portions of the shaft coupler are uncoupled according to the disclosure.

FIG. 15D is an illustration of the vacuum lance system of FIG. 15A in another of many activated positions wherein the opening in the release is sealed according to the disclosure.

DETAILED DESCRIPTION OF THE INVENTION

Figure 1:
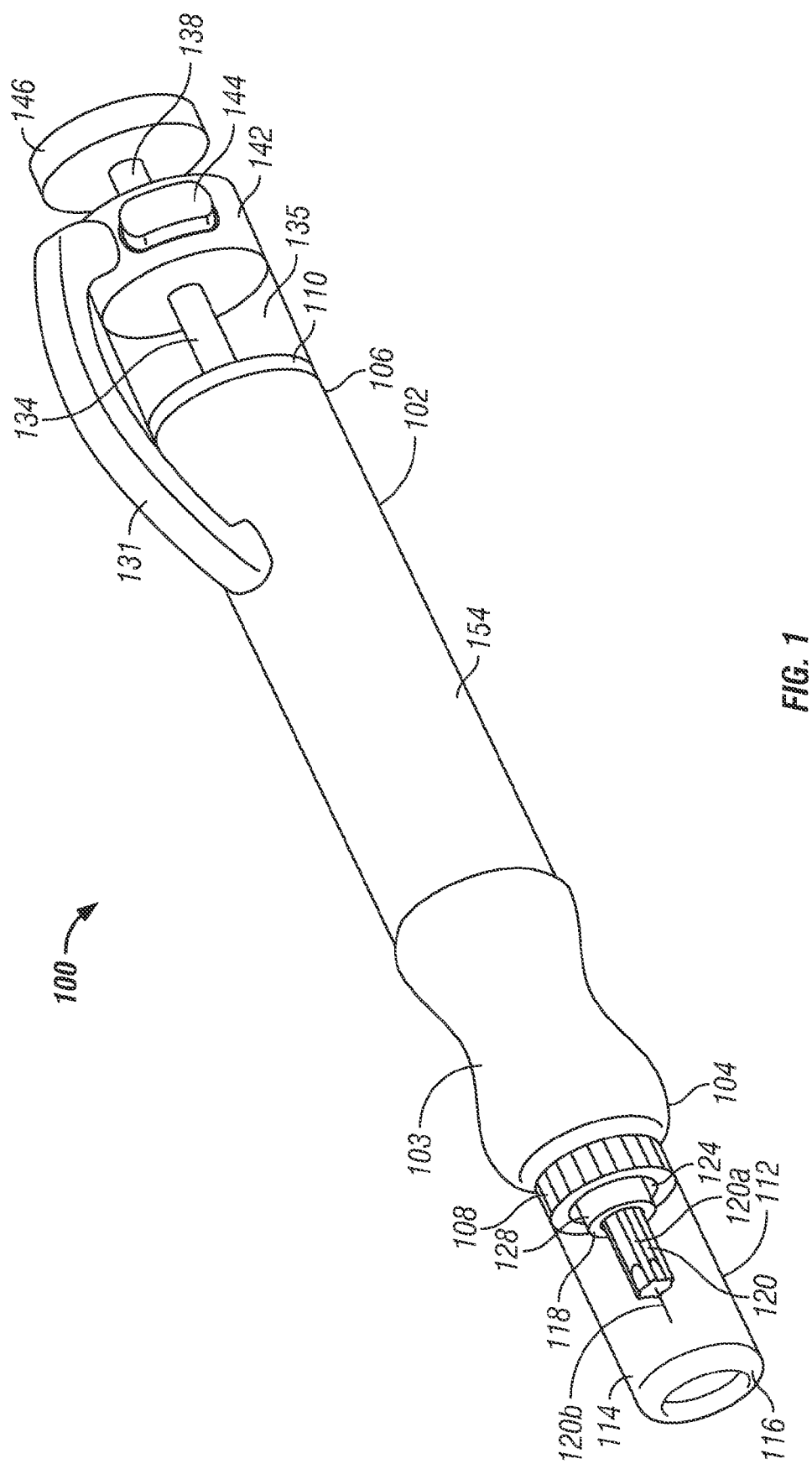
FIG. 1 is an isometric schematic view of one of many embodiments of a vacuum lance system according to the disclosure.

The Figures described above and the written description of specific structures and functions below are not presented to limit the scope of what Applicant has invented or the scope of the appended claims. Rather, the Figures and written description are provided to teach any person skilled in the art to make and use the invention for which patent protection is sought. Those skilled in the art will appreciate that not all features of a commercial embodiment of the invention are described or shown for the sake of clarity and understanding. Persons of skill in this art will also appreciate that the development of an actual commercial embodiment incorporating aspects of the present invention will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location, and from time to time. While a developer's efforts might be complex and time-consuming in an absolute sense, such efforts would be, nevertheless, a routine undertaking for those of ordinary skill in this art having benefit of this disclosure. It must be understood that the invention disclosed and taught herein is susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims. When referring generally to such elements, the number without the letter is used. Further, such designations do not limit the number of elements that can be used for that function. The terms "couple," "coupled," "coupling," "coupler," and like terms are used broadly herein and can include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and can further include without limitation integrally forming one functional member with another in a unity fashion. The coupling can occur in any direction, including rotationally.

This disclosure provides a vacuum assisted lancing system and method that can be easily used at a wide variety of places on a human or animal, even in places with less sensitivity, such as the stomach, sides, arms and legs. The system can be used with one hand and is easily portable. The system can minimize pain due to its ability to operate on unconventional areas on a user, and in at least one embodiment minimizes pain due to vibration during lancing. The term "user" and like terms are used broadly herein and include, without limitation, a person who uses the present invention on his/her self, or a person (or animal) for whom another person uses the present invention to lance the person (or animal). The system's vibration can at least partially mask any pain from a patient during lancing. Further, the lance itself can be easily replaced from a position external to the system with simple insertion. Not requiring batteries, nor containing any form of motor, the system is virtually maintenance free, other than replacement of the lance after use and occasional common cleaning. The system can be easily carried to be readily available wherever the user needs to take a blood sample. Integration of this system into the common mainstream method of blood glucose measurement can be significantly assisted because the system draws from the same pool of body blood as other devices. Therefore, special glucose measuring instruments and supplies may not be required, and blood measurement procedures may not have to be altered from those currently in practice.

Figure 2:
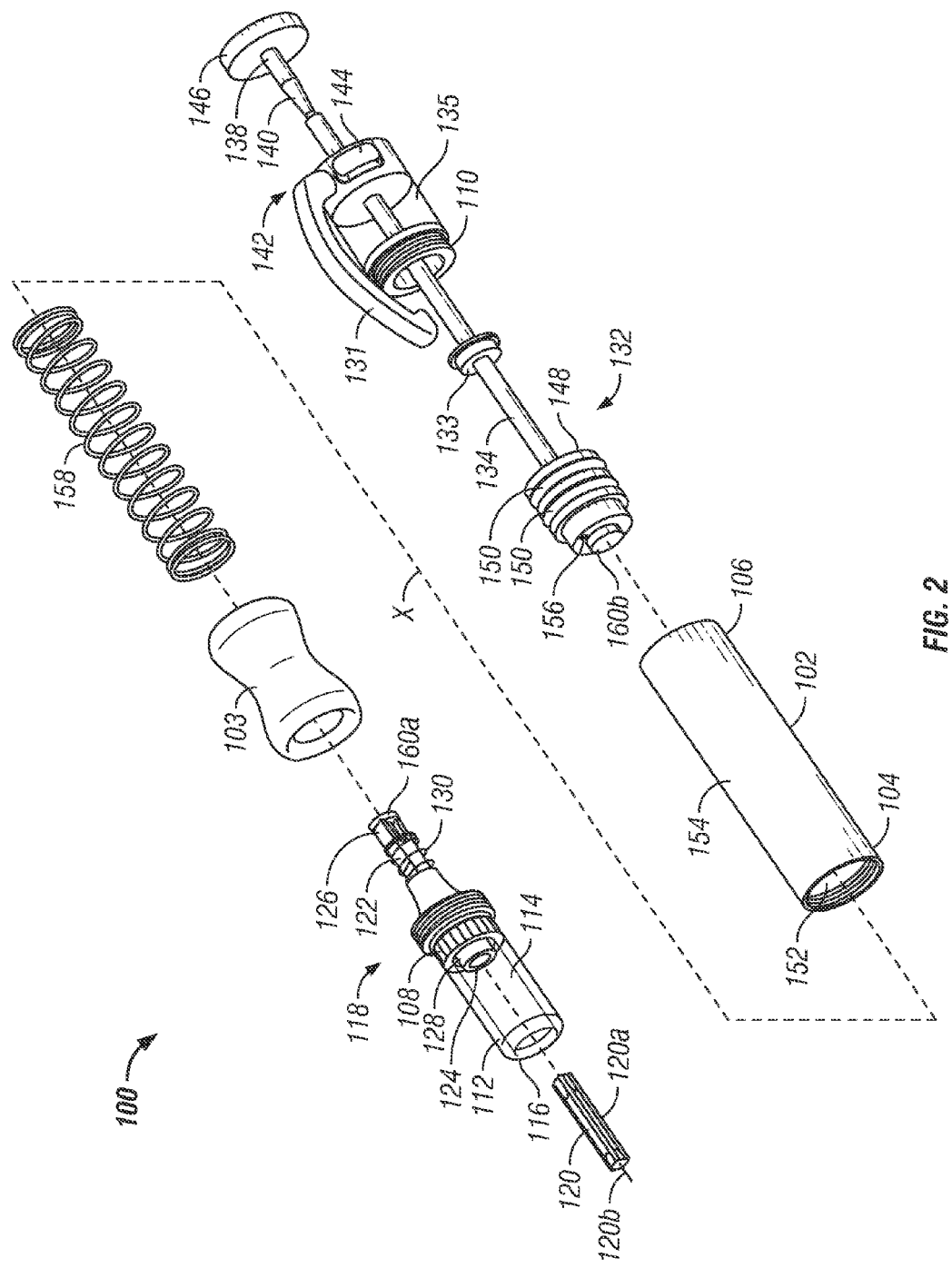
FIG. 2 is an isometric assembly schematic view of the vacuum lance system of FIG. 1.

FIG. 1 is an isometric schematic view of one of many embodiments of vacuum lance system 100 according to the disclosure. FIG. 2 is an isometric assembly schematic view of the vacuum lance system of FIG. 1. FIG. 3A is a cross-sectional schematic view of another of many embodiments of vacuum lance system 100 having an indicator 133 according to the disclosure. FIG. 3B is a cross-sectional schematic view of the indicator 133 of FIG. 3A in viewing window 135. FIG. 4 is a cross-sectional schematic view of one of many embodiments of lancing mechanism 118 according to the disclosure. FIGS. 1-4 will be described in conjunction with one another. Vacuum lance system 100 can include a device body 102, which can comprise, for example, a tubular vacuum body, for supporting one or more components for lancing. Device body 102 can have a bottom lancing end 104 and a top free end 106, and can, but need not, be transparent, in whole or in part. Device body 102 can be formed from any material, such as plastic, metal, or another material, separately or in combination, and can be any size required by a particular application. System 100 can, but need not, include a grip 103, such as a foam, rubber, plastic, or other holder, for holding the system. System 100 can, but need not, include a holder 131, such as a belt clip, pocket clip, loop, or other holder, for supporting the system, for example, when not in use.

System 100 can include one or more components for lancing (the components collectively referred to herein as a lancing assembly), which can include one or more components for vacuuming, coupled to device body 102. System 100 can include a lance guide 112, such as a tube, coupled to lancing end 104, such as for "aiming" system 100 or for contacting a lancing surface, such as skin, for lancing, directly or indirectly. Lance guide 112 can be any size required by a particular application, and can advantageously include a viewing area 114 for viewing the surface being lanced. Viewing area 114 can be a "window" coupled to the wall of lance guide 112, or as another example, lance guide 112 can be transparent, in whole or in part. Lance guide 112 can, but need not, have a seal 116, such as an annular seal coupled to its bottom end for sealing against a surface being lanced or, as another example, for at least reducing discomfort to a user when system 100 is pressed against an area of the user's body for lancing. Seal 116 can be, for example, a rounded or contoured edge, a soft coating, such as a rubber coating, a pad, a gasket, or another seal, in whole or in part. As another example, in at least one embodiment, which is but one of many, seal 116 can be a suction cup (see, e.g., FIG. 9). Seal 116 can, but need not, be flexible. For example, seal 116 can have an amount of flexibility, so that lance system 100 does not have to be held substantially perpendicular to a lancing surface to assure sealing engagement with the surface. Seal 116 can, but need not, include or be formed from, in whole or in part, a material that has gripping properties, for example, so that if the seal is moved or rotated while in contact with a surface, such as skin, the surface concurrently moves or rotates.

With further reference to FIGS. 1 and 2, system 100 can include a lancing mechanism 118 coupled to lancing end 104, for example, to end cap 108, for supporting a lance 120 (also known as a "lancet"). Lance 120 can include a lance base 120a for supporting a lance needle 120b. Lancing mechanism 118 can include a lancing shaft 122 slideably coupled with end cap 108, such as along central longitudinal axis X, for communicating lance 120 with a surface during lancing. Lancing shaft 122 can include a bottom lance coupling end 124 and a top actuating end 126, and can be any length required by a particular application, as will be further described below. Lancing mechanism 118 can include a lance coupler 128 coupled to lance coupling end 124 for coupling lance 120 to shaft 122, removably or otherwise. For example, lance coupler 128 can be tubular and can form an interference or friction fit with lance base 120a. Lance coupler 128 can, but need not, be adjustable, such as by having a slot or notch at least partially along its length, for example, for coupling to lances of one or more sizes or shapes. As other examples, lance coupler 128 can include threads, screws, notches, or other fasteners for coupling to a lance, as will be understood by one of ordinary skill in the art. Lancing mechanism 118 can include one or more biasing devices, such as a lancing spring 130. Lancing spring 130 can be coupled to lancing shaft 122 for biasing shaft 122 in one or more directions, temporarily, momentarily or otherwise, as will be further described below. Lancing spring 130 can, but need not, comprise a plurality of springs, and can advantageously include two springs.

System 100 can include a vacuum mechanism 132 for creating a vacuum and communicating with lancing mechanism 118 or other components of system 100. Vacuum mechanism 132 can include a main shaft 134 having a bottom main actuating end 136, a top main free end 138, and at least one release coupler 140, such as, for example, a notch or indention. Main shaft 134 can be slideably coupled with top end cap 110, for example, so that main actuating end 136 can be disposed inside device body 102 and main free end 138 can be disposed outside device body 102. System 100 can, but need not, include a knob 146, such as a button or cap coupled to main free end 138, for manipulating main shaft 134 or other components. System 100 can include a release mechanism 142, such as a firing device, for communicating with main shaft 134, for example, for releasably coupling with release coupler 140, a series of release couplers, or another portion of main shaft 134. Release mechanism 142 can be any type of releasable coupler, adapted to cooperate with main shaft 134, as will be understood by one of ordinary skill in the art. For example, release mechanism 142 can couple with main shaft 134 at one or more positions along its length, such as with release coupler 140, a series thereof or, for example, a notch, groove or outer surface, to releasably hold main shaft 134 in a particular position until, for example, release 144 is actuated, as will be further described below. Vacuum mechanism 132 can include a piston 148 coupled to main shaft 134 for communicating with one or more other components of system 100 to create a vacuum. Piston 148 can be coupled, adjustably, fixedly or otherwise, anywhere on main shaft 134 inside of device body 102, such as, for example, to main actuating end 136. Piston 148 can, but need not, include one or more seals, such as one or more O-rings 150, and can sealingly communicate with interior wall 152 of device body 102, which can, for example, form a vacuum chamber 154 inside device body 102 between piston 148 and a surface to be lanced in communication with seal 116.

System 100 can include one or more openings 156, such as an air passage or orifice, for fluid communication between vacuum chamber 154 and an atmosphere surrounding the vacuum chamber. Opening 156 can be calibrated to allow air to flow into vacuum chamber 154 at a predetermined vacuum dissipation rate, such as, for example, a vacuum dissipation rate less than a predetermined vacuum generation rate in vacuum chamber 154. Opening 156 can be any suitable place for communicating with a vacuum in system 100, such as in device body 102 (see, e.g., FIG. 9), and can advantageously, but need not, be in piston 148, separately or in combination. Each opening 156 can, but need not, be adjustable in size, which may include having an adjustable diameter or being interchangeable, separately or in combination. One or more openings 156 can afford any rate of vacuum dissipation required by a particular application, such as a linear rate, non-linear rate, or another rate, in whole or in part, separately or in combination.

Vacuum mechanism 132 can include a biasing device, such as vacuum spring 158, coupled to piston 148 for biasing piston 148 in one or more directions, such as in the upward direction. Vacuum spring 158 can, but need not, include a compression spring disposed between bottom end cap 108 and piston 148 that biases the piston away from bottom end cap 108. Alternatively, or collectively, for example, vacuum spring 158 can include a tension spring that biases piston 148 toward top end cap 110, such as a tension spring disposed between piston 148 and top end cap 110, as will be understood by one of ordinary skill in the art having the benefits of this disclosure. Vacuum spring 158 can, but need not, include a plurality of springs.

System 100 can include a vacuum indicator 133 for indicating whether or to what extent a vacuum exists within vacuum chamber 154. For example, indicator 133 can indicate when a vacuum having at least a predetermined magnitude is present in the system or, as another example, when a vacuum below the predetermined magnitude can be present, including when no vacuum is present. In at least one embodiment, which is but one of many, indicator 133 can be a visual indicator, such as a tab, mark, colored media, notch, or other visible indicator, coupled to main shaft 134, piston 148, or another component, so that indicator 133 can visually indicate, such as by being visible, when no vacuum or a vacuum below a predetermined magnitude is present in the system. Indicator 133 can be visible, for example, through a slot, window, portion of device body 102, or other transparent media, which can be any size or shape. As shown in FIGS. 3A and 3B, for example, indicator 133 may not be visible, such as being inside device body 102, while a vacuum having a predetermined magnitude can be present in the system, and can become visible, such as by passing through a portion of free end 106 and into indicator window 135 when no vacuum or a vacuum below a predetermined magnitude is present in the system. As another example, indicator 133 can be visible through at least a portion of device body 102, through an elongated window disposed longitudinally along device body 102, or through a combination thereof. Alternatively, indicator 133 need not be visible through device body 102 and can be visible only when outside of device body 102, in whole or in part (see, e.g., FIGS. 5A-5E). For example, and without limitation, indicator 133 can be a marking on shaft 134 which only becomes visible outside of device body 102 (e.g., above release mechanism 142) when shaft 134 has sufficiently exited free end 106, so as to indicate that the vacuum has fallen below a predetermined value. In at least one of many alternative embodiments, indicator 133 can be an audible indicator, digital indicator, electrical indicator, electronic indicator or, as other examples, a pressure sensitive indicator or mechanical indicator, separately or in combination. Indicator 133 can, but need not, indicate to a user when a vacuum in system 100 during lancing is sufficiently dissipated (i.e., is of sufficiently low magnitude) that system 100 can be removed from a surface being lanced. For example, in an application where skin is being lanced for purposes of drawing blood, indicator 133 can indicate when system 100 can be removed from the skin so that the drawn blood does not splatter, such as could happen due to an inrush of atmospheric air, e.g., if seal 116 were to be lifted off the skin with a relatively high vacuum in vacuum chamber 154.

System 100 can include a shaft coupler 160 for releasably coupling one or more components of system 100, such as lancing shaft 122 and main shaft 134. Shaft coupler 160 can include two or more portions that optionally couple with one another. For example, shaft coupler 160 can include a first portion 160a coupled to lancing shaft 122, such as to actuating end 126, and a second portion 160b coupled to main shaft 134, such as to main actuating end 136. First portion 160a and second portion 160b can be adapted to releasably couple to one another when brought at least proximate to one another and to uncouple upon a predetermined event, for example, when a sufficient force applied to shaft coupler 160. In at least one embodiment, which is but one of many, one of portions 160a, 160b can be a magnet and the other portion can be magnetic material, which can allow, for example, lancing shaft 122 and main shaft 134 to remain coupled until a separation force, such as a tensile force, is applied sufficient to overcome the coupling force between first portion 160a and second portion 160b. Alternatively, or collectively, either portion 160a, 160b can be a portion of one of the shafts 122, 134, such as one of the actuating ends 126, 136, or, as another example, second portion 160b can be coupled to, including formed integrally with, piston 148. In at least one other embodiment, which is but one of many, first and second portions of shaft coupler 160 can include hook and loop material, mechanical fasteners, ball and joint unions, sticky material, or other couplers, as required by a particular application. In at least one embodiment, which is but one of many, a sufficient separation force can be any force less than a force generated by the vacuum spring 158 (see, e.g., FIG. 2).

With reference to FIG. 4, lancing mechanism 118 can, but need not, include bottom end cap 108. Alternatively, lancing mechanism 118 can be separately coupled to bottom end cap 108 or another portion of lancing end 104 of device body 102. Lancing spring 130 can include a plurality of springs, such as upper spring 130a and lower spring 130b (collectively referred to herein as lancing spring 130). Lancing mechanism 118 can include a stop 129, such as a tab or block, for supporting lancing spring 130 or defining the stroke of lancing shaft 122, in whole or in part. In at least one embodiment, such as the embodiment shown in FIG. 4, which is but one of many, stop 129 can be disposed between lance coupling end 124 and actuating end 126 of lancing shaft 122. Upper spring 130a can be coupled between stop 129 and actuating end 126, and lower spring 130b can be coupled between stop 129 and lance coupling end 124. Each lancing spring 130a, 130b can be loosely disposed about shaft 122 or can have one or more ends fixedly coupled to shaft 122 or stop 129, separately or in combination. Each lancing spring 130a, 130b can be any type of spring, or other biasing device, and can have any K value or length required by a particular application. Lancing shaft 122 can have a resting state, which can be at least partially defined by communication between springs 130a, 130b and stop 129, separately or in combination with one or more other components of system 100. For example, when shaft 122 is at rest, one or more of springs 130a, 130b can, but need not, be in their natural state (i.e., neither compressed nor extended). Alternatively, one or more springs can be under tension or compression when lancing shaft 122 is at rest or, as another example, while lancing shaft 122 is in motion, such as during lancing, as required by a particular application and as will be understood by one of ordinary skill. When lancing shaft 122 is in a rest position, lance needle 120b can, but need not, be distal from a surface 168 being lanced, such as skin (see, e.g., FIG. 5F). Lancing shaft 122 can be any length required by a particular application and can be slideably coupled with stop 129 so that lancing spring 130 can bias shaft 122, such as in the upward or downward direction, as will be further described below.

FIG. 5A is an illustration of one of many embodiments of a vacuum lance system 100 in a cocked position according to the disclosure. FIGS. 5B, 5C and 5D are illustrations of the system 100 of FIG. 5A in three respective positions during lancing.

Figure 5H:
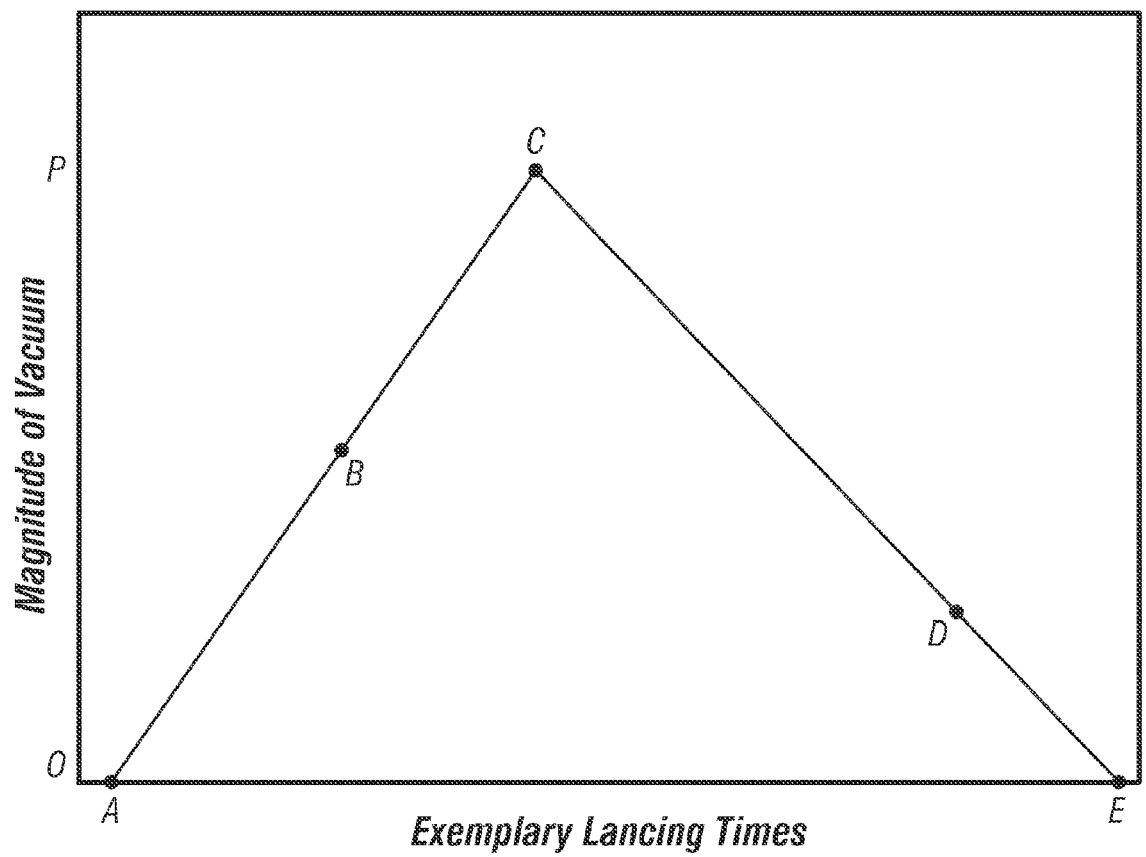
FIG. 5H is a graph illustrating one example of the vacuum magnitude versus the time over which lancing can occur during a vacuum cycle according to the disclosure.

FIG. 5E is an illustration of the system 100 of FIG. 5A in an uncocked position. FIG. 5F is an illustration of the system 100 of FIG. 5A manipulating a surface during lancing. FIG. 5G is an illustration of the system 100 of FIG. 5A vibrating a surface during lancing. At least one of many methods of using the embodiment of system 100 shown in FIGS. 5A-5G can be described. FIG. 5H is a graph illustrating the vacuum magnitude versus the time over which lancing can occur during a vacuum cycle. FIGS. 5A-5H will be described in conjunction with one another.

A lance 120 can be coupled to lancing mechanism 118, such as by using one of the methods described herein, for example, before or after system 100 is in a "cocked" position (see, e.g., FIG. 5A). System 100 can be cocked, for example, by pressing knob 146 downward until at least a portion of main shaft 134, such as release coupler 140, couples with release mechanism 142, which can releasably hold main shaft 134 and piston 148 downwardly toward lancing end 104, such as against the force of vacuum spring 158. Shaft coupler second portion 160b on main actuating end 136 can couple to first portion 160a of shaft coupler 160 on actuating end 126 of lancing shaft 122. Actuating end 126 can, but need not, move downwardly during cocking, temporarily or otherwise. Upper spring 130a and lower spring 130b can, but need not, be in their natural states. System 100 can engage a surface to be lanced (not shown), such as to an area of skin on a person's body, which can be any area. For example, seal 116 on lance guide 112 can engage the surface so that at least a partially airtight seal is formed between seal 116 and the surface.

System 100 can be activated, or fired, for example, by actuating release 144, which can at least partially uncouple main shaft 134 and, for example, release coupler 140, from release mechanism 142, which can allow main shaft 134 to slideably communicate with top end cap 110. Release 144 can be pressed directly, such as with a user's finger, or indirectly actuated, for example, using a magnet, electrical or mechanical actuator, or another method, as required by a particular application. Vacuum spring 158 can at least partially decompress (or lose tension if a tension spring, as mentioned above and further described below) and piston 148, main shaft 134 and shaft coupler 160 can move in the upward direction away from the surface being lanced. Piston 148, which can, but need not, include one or more seals, such as O-rings 150, can be in sliding sealing engagement with interior wall 152 of device body 102, thereby at least partially forming a vacuum in vacuum chamber 154 as piston 148 moves away from the surface being lanced. One or more components of lancing mechanism 118, such as actuating end 126 and lancing shaft 122 can move upward with main shaft 134, for example, due to the coupling force of shaft coupler 160 and the force of expanding vacuum spring 158. Upper spring 130a can expand and lower spring 130b can contract, which can, for example, singularly or in combination, exert an increasing force on first portion 160a of shaft coupler 160 in the opposite direction (e.g., downward) of the force exerted on second portion 160b by vacuum spring 158 (e.g., upward) as vacuum spring 158 expands (FIG. 5B). Lancing shaft 122 can have a shorter stroke than main shaft 134. For example, stop 129 can limit the stroke of lancing shaft 122, for example, by preventing at least a portion of shaft 122 from traveling upward past the stop or, as another example, lancing spring 130 (referring collectively to springs 130a and 130b) can be arranged to limit the stroke of lancing shaft 122, separately or in combination with stop 129. In at least one embodiment, which is but one of many, lancing spring 130 can have, for example, a length or K-value that can result in a lancing spring force greater than the coupler force of shaft coupler 160 when lancing shaft 122 is in a particular position, which can be any position required by a particular application.

Shaft coupler 160 can uncouple and second portion 160b can continue moving in the upward direction (FIG. 5C). Piston 148 can continue moving upward during and after penetration of the surface, continuously or in segments, such as by using two or more release couplers 140 that successively couple to release mechanism 142, which can increase the vacuum to which the surface can be exposed. Upper spring 130a can contract and lower spring 130b can expand, singularly or in combination, which can, for example, cause first portion 160a to move in the opposite (i.e., downward) direction from second portion 160b of shaft coupler 160. Lancing shaft 122 may be drawn back away from the surface and the coupling force between portions 160a and 160b may be overcome. Lancing mechanism 118 can move toward a rest position, such as due to the force of one or more springs 130. Lancing shaft 122 can move downwardly, such as until at least a portion of lance 120 contacts the surface (FIG. 5D). In at least one embodiment, which is but one of many, lancing shaft 122 can, but need not, move downwardly far enough that upper spring 130 at least partially compresses and lower spring 130b at least partially expands as lance 120 lances the surface. As will be understood by one of ordinary skill, inertia may cause lancing shaft 122 to move past its rest position (e.g., downward), for example, so that lance needle 120b may pierce the surface, before returning to its rest position. After at least partially penetrating the surface, each of springs 130a, 130b and lancing shaft 122 can return to a state of rest (FIG. 5E), and lance 120 can be disposed upwardly and distally from the surface.

The surface can be subjected to a vacuum before, during, or after lancing, separately or in combination. Air can enter vacuum chamber 154 (selectively, automatically, or otherwise), such as through opening 156, which can dissipate the vacuum at any rate required by a particular application. Indicator 133, such as a tab, groove, or mark, can become visible, such as by passing outside of device body 102, which can indicate dissipation of the vacuum, in whole or in part. System 100 can be disengaged from the surface, which can leave a quantity of blood on the surface for collection.

A surface 168 being lanced can, but need not, be manipulated during lancing, which can include twisting, pumping, pressing up and down, or any movement, separately or in combination (see, e.g., FIG. 5F). For example, where surface 168 is skin, one or more components on lancing end 104 of device body 102, such as lance guide 112 or seal 116, can be used to knead, massage or otherwise manipulate the skin at any time during the lancing process, for example, before, during or after the skin is lanced, which can result in a greater volume of blood 176 being extracted and/or more rapid blood extraction. As an example of this manipulation, seal 116 can be placed against the skin and twisted in one or more directions, such as back and forth, clockwise, then counterclockwise (or vice versa), for example, so that the skin twists, such as due to friction between the skin and seal 116, which can increase blood flow to the area being lanced or out of an opening in the skin made by lance 120. The surface of seal 116 can be made of or coated with a gripping type substance, such as to aid in twisting the surface when seal 116 is being twisted. Another example of this manipulation, which can speed up blood drawing, can include increasing and decreasing inward pressure of seal 116 on the surface in a pulse-like action. Each of these classes of manipulation, just as with squeezing a finger if it is pricked, can speed up blood flowing through a lance-generated hole. This can be especially true in the presence of a vacuum on the surface as described in the present disclosure. The degree of manipulation, if any, of the skin can vary from surface to surface on areas of the user, and from user to user, as will be understood by one of ordinary skill having the benefits of this disclosure.

With continuing reference to FIGS. 5A-5G, and further reference to FIG. 5H, the timing and magnitude of vacuum creation and lancing can include one or more variables, as will be understood by one of ordinary skill, each of which can have any value required by a particular application. The magnitude of the vacuum and the rate at which the vacuum can be created, the timing of lancing, such as when shaft coupler 160 uncouples, the rate at which lance 120 can travel, and the force with which lance 120 strikes a surface, or other factors can, but need not, be optimized for a particular application. Further, the vacuum creation can occur in a single stage, or in multiple stages. For example, one or more of these factors can be correlated with travel and timing of the piston 148 along a length of device body 102. As will be understood by one of ordinary skill in the art, the further piston 148 travels within device body 102 (e.g., away from a surface being lanced), the higher a vacuum in vacuum chamber 154 may be. Further, the force with which lance 120 contacts a surface, such as skin, can be at least enough to puncture or penetrate the surface, and can advantageously drive at least a portion of needle 120b through the surface and into subcutaneous tissue beneath the surface from which blood may be taken. One or more variables can be defined by the length and/or K value of a spring, such as of lancing spring 130 or vacuum spring 158, the volume of vacuum chamber 154 or, as another example, by the weight, stroke or length of a shaft, such as lancing shaft 122 or main shaft 134.

In at least one embodiment, such as the embodiment shown in FIGS. 5A-5G, which is but one of many, the stroke of lancing shaft 122 can determine when shaft coupler 160 can uncouple during lancing and when lance 120 can contact or penetrate the surface being lanced, such as during a period of time in which a vacuum can be applied to the surface. For example, upon release from a cocked position, piston 148 can travel upward from a lowermost position (see, e.g., FIG. 5A) where no vacuum exists within vacuum chamber 154 to an uppermost position (see, e.g. FIG. 5E), thereby creating a maximum vacuum within vacuum chamber 154, which can be any magnitude of vacuum, such as up to 30 inches of mercury, required by a particular application.

As shown for illustrative purposes in FIG. 5H, lancing of a surface can occur at any time before, during, or after a vacuum cycle, as may be suitable for a particular application. For example, the lancing of the surface can occur before a vacuum is created, as indicated by reference A. Alternatively, the lancing of the surface can occur while the vacuum is increasing in the device body, as indicated by reference B, such as at ½ of peak vacuum P. As will be understood by one of ordinary skill having the benefits of this disclosure, reference B illustrates one of many lancing times during vacuum creation, and lancing can alternatively occur at any point along a line between references A and C. The lancing can also occur when the vacuum is at peak vacuum P, illustrated by reference C. In one or more other embodiments, lancing may occur after peak vacuum and before the vacuum has been entirely dissipated, such as at a point in time illustrated by reference D, which may be, for example, 1/3P, or any point in time along a line between references C and E. As another example, lancing may occur after a vacuum has dissipated, such as at the point in time illustrated by reference E.

As described above, lancing can occur at any time during a vacuum cycle, including before, during, or after a vacuum is created, and can advantageously occur when at least a partial vacuum is created, such as between 30% and 70%, or any increment there between, of the maximum vacuum for a particular application. In at least one embodiment, which is but one of many, lancing can advantageously occur at between 40% and 60% of vacuum creation, or any increment there between, such as at 50% vacuum creation. For example, the maximum vacuum can be −20 in Hg, and the surface can be lanced when the vacuum in vacuum chamber 154 is, for example, −10 in Hg. However, this need not be the case, and the examples described herein are for illustrative purposes. The timing of lancing can, but need not, be adjustable. For example, in at least one embodiment, such as a commercial embodiment, which is but one of many, system 100 can include a plurality of interchangeable lancing shafts, each of which can have a different length, which can determine when lancing occurs during a vacuum cycle, as described above.

The rate at which the vacuum is created, which can be at least partially determined by the rate at which piston 148 travels upward, can, but need not, be adjustable. For example, in at least one embodiment, system 100 can include a shock absorber, piston or other device (not shown), for controlling the rate at which piston 148 ascends during lancing. The vacuum can be dissipated, or released, such as through opening 156, or movement of piston 148, separately or in combination, at any rate and at any time required by a particular application. For example, where the surface being lanced is skin, the vacuum can advantageously be released at a rate and time that may allow an adequate amount of blood for collecting to be drawn from the surface or, as another example, at a rate that can at least partially minimize blood splatter when the system is removed from the skin.

With continuing reference to FIGS. 5A-5G, system 100 can, but need not, be adapted to vibrate during lancing. The term "vibrate" and conjugations thereof are used broadly herein and specifically include, without limitation, any shake, quiver, pulsation, or other movement applied by lance system 100 to a surface being lanced. One or more vibrations can be timed to occur in proximity (e.g., in time and space) to lance penetration of a surface, which can mask the sensation of penetration from the user. Vibration in system 100 can at least partially mask pain associated with lancing, if any, such as where the surface being lanced is skin. The vibration can be controlled by adjusting properties of one or more of the components, such as the dynamic components, of a particular embodiment of system 100, and can have any magnitude or duration required by a particular application. The magnitude of a vibration can depend on, or be predetermined by, for example, the mass of one or more components in the system, the K value of one or more springs, the stroke of one or more shafts, the momentum of one or more components, or other factors, as will be understood by one of ordinary skill having the benefits of this disclosure. One or more vibrations can occur singularly, consecutively, concurrently, supplementary or otherwise, and can occur in, or transfer to, one or more components of system 100. Advantageously, one or more vibrations may be present at lancing end 104, for example, so that the vibrations can at least partially transfer to surface 168 during lancing (see, e.g. FIG. 5G), which can thereby aid in masking the pain of lancing. The vibration can be caused by any of the components, such as the dynamic components, of a particular embodiment of system 100, and can have any magnitude or duration required by a particular application. The magnitude of a vibration can depend on, or be predetermined by, for example, the mass of one or more components in the system, the K value of one or more springs, the stroke of one or more shafts, the momentum of one or more components, or other factors, as will be understood by one of ordinary skill having the benefits of this disclosure. In at least one embodiment, which is but one of many, a vibration can begin before penetration of a surface, and can, at least partially, continue during penetration of the surface. The vibration can advantageously, but need not, continue after the surface has been lanced. As other examples, one or more components of lancing mechanism 118, such as lancing spring 130 or lancing shaft 122, can cause vibration in system 100, separately or in combination with other components in the system.

In at least one embodiment, which is but one of many, one or more portions of the lancing assembly, such as lancing shaft 122, lance coupler 128, or main shaft 134, can move in a first direction, such as toward free end 106 of device body 102, for example, over a first distance. One or more of the portions, such as first portion 160a of shaft coupler 160, can be stopped from moving further in the first direction, such as further than the first distance, for example, by stop 129, which can cause a vibration in one or more parts of system 100. Advantageously, the vibration continues to occur for an amount of time at least long enough for the surface to be penetrated. One or more components can move in a second direction, such as in a direction opposite the first direction, for example, toward the lancing end 104 of device body 102. The one or more components, such as lancing shaft 122 or first portion 160a of shaft coupler 160, can be stopped from further moving in the second direction, for example, past a second distance, which can cause one or more vibrations in system 100.

Figure 6:
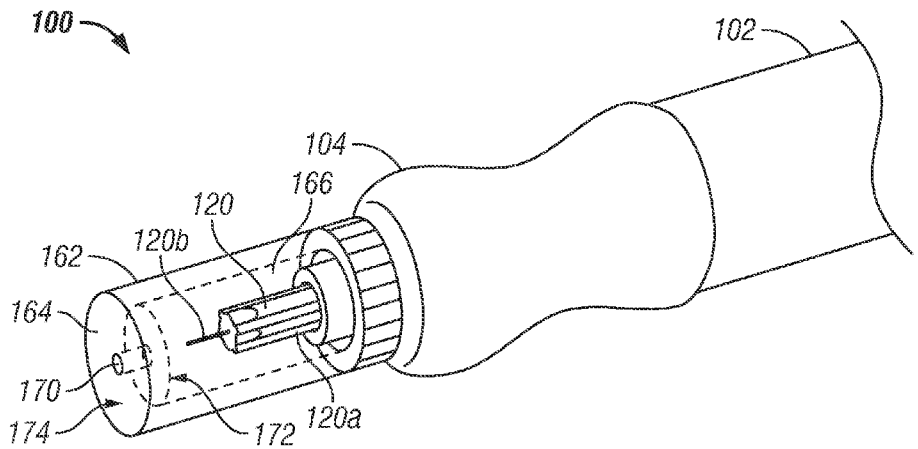
FIG. 6 is a front isometric schematic view of one of many embodiments of a vacuum lance system having a depth controller according to the disclosure.
Figure 7A:
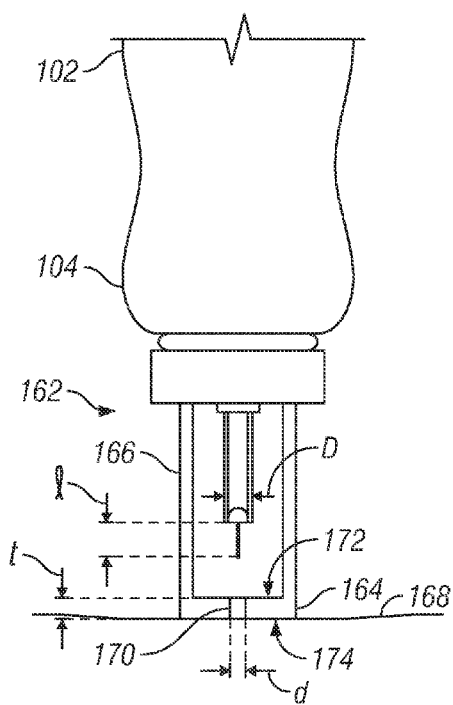
FIG. 7A is a cross-sectional schematic view of the system of FIG. 6.
Figure 7B:
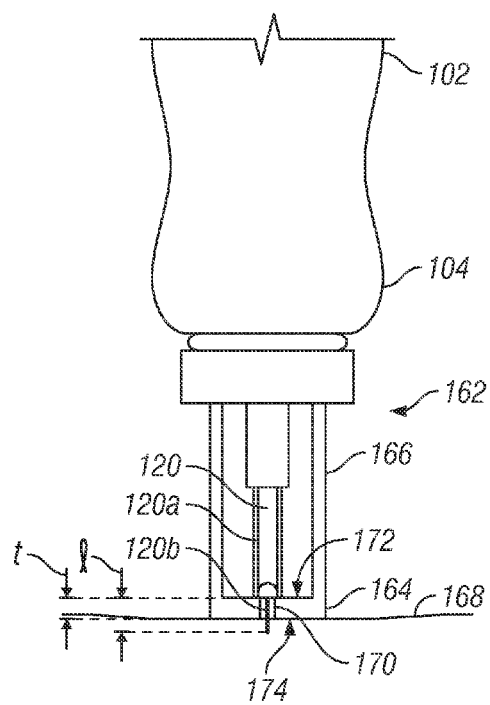
FIG. 7B is a cross-sectional schematic view of the system of FIG. 6 with a base contacting a spacer.
Figure 7C:
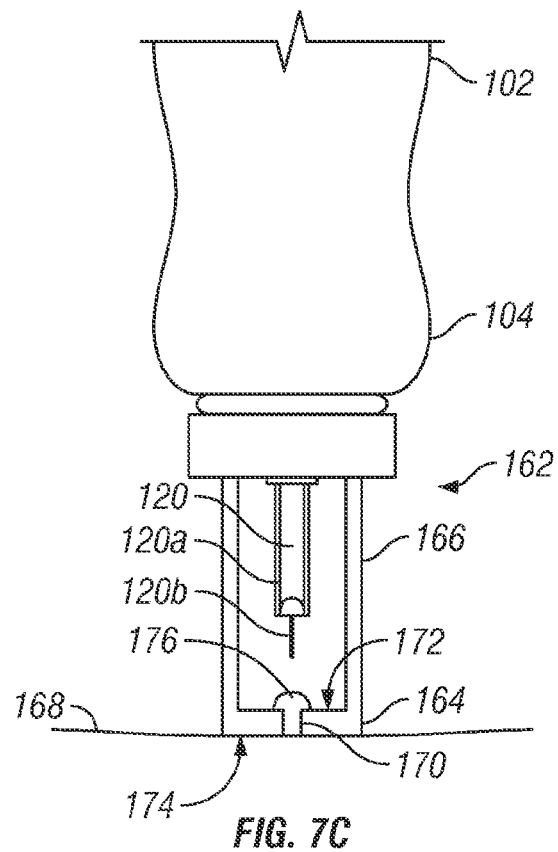
FIG. 7C is a cross-sectional schematic view of the system of FIG. 6 during blood extraction.

FIG. 6 is a front isometric schematic view of one of many embodiments of vacuum lance system 100 having a depth controller 162 according to the disclosure. FIG. 7A is a cross-sectional schematic view of the system 100 of FIG. 6. FIG. 7B is a cross-sectional schematic view of the system 100 of FIG. 6 with a base contacting a spacer. FIG. 7C is a cross-sectional schematic view of the system 100 of FIG. 6 during blood extraction. FIGS. 6-7C will be described in conjunction with one another. Vacuum lance system 100 can include a depth controller 162 for controlling the depth to which a surface is lanced during lancing. Depth controller 162 can include a calibrated spacer 164 and a spacer coupler 166 for coupling spacer 164 to lancing end 104 of device body 102. Depth controller 162 can be formed from any material, such as plastic or metal, and can be replaceably and interchangeably coupled to device body 102 in any manner, such as being threaded thereon, forming an interference or friction fit with one or more other components of system 100, or fastened with fasteners, such as screws, brackets, adhesive, or other fasteners, removably, permanently or otherwise, and other method of attachment. Alternatively, depth controller 162 can be fixedly coupled to device body 102, integrally or otherwise, or any portion thereof. Depth controller 162 can, but need not, be transparent, in whole or in part. Spacer coupler 166 can be tubular and can be coupled, for example, to lance guide 112 (see, e.g., FIG. 1) or, as another example, in place of lance guide 112, as required by a particular application. Spacer 164 can be coupled to spacer coupler 166, including being formed integrally therewith, between lance 120 and a surface 168 being lanced. As another example, depth controller 162 can be adjustable, such as by way of one or more variable components, for example, a spacer 164 of varying length or thickness, as will be further described below (see, e.g., FIG. 18).

Spacer 164 can include a central opening, such as hole 170, for allowing at least a portion of lance 120 to pass there through, and can have a calibrated thickness 't', which can be any thickness required by a particular application, and which can be the same or different from the thickness of one or more portions of spacer coupler 166. Spacer 164 can, but need not, be adjustable, which can include being interchangeable, individually or simultaneously with spacer coupler 166, for example, to allow for spacers of different thicknesses. Hole 170 (having dimension "d" in FIG. 7A) can have any shape or cross-sectional area required by a particular application, and can advantageously have a cross-sectional area larger than that of needle 120b and smaller than that of base 120a (having dimension "D" in FIG. 7A) so that needle 120b can pass through hole 170 and base 120a can not, i.e., D>d (see, e.g., FIG. 7B). Base 120a can contact the upper surface 172 of spacer 164 during lancing, which can limit the depth to which needle 120b can penetrate surface 168, such as to the difference between length "l" of needle 120b and the thickness "t" of spacer 164. This can be advantageous, for example, because the depth of penetration of needle 120b into surface 168 can be controlled regardless of the force with which lance 120 travels in the downward direction during lancing, which can be any force. For example, where the surface 168 is skin, the force required to thrust lance 120 into the skin can vary from application to application and user to user, such as between relatively soft or thin skin and relatively tough or thick skin, such as, for example, calloused skin.

Depth controller 162 can allow, for example, a relatively large force, such as a force large enough to lance calloused skin, to also be used on softer areas of skin, for example, by stopping the travel distance of needle 120b, so that regardless of its toughness, skin can be lanced to a depth of "l" minus "t" when the bottom surface 174 of the spacer 164 is adjacent the skin, i.e., a depth equal to the difference between the length "l" of lance needle 120b and the thickness "t" of spacer 164. As another advantageous example, where the surface 168 being lanced is skin, a blunt force or vibration can result, such as from an impact between upper surface 172 and base 120a, which can, but need not, mask pain that can result from lancing. In at least one embodiment, which is but one of many, and is described herein only for illustrative purposes, lance 120, which can, but need not, be an off-the-shelf commercially available lance, can have a base 120a having a dimension "D" (which can, but need not, be a diameter) of 0.250" and a lance needle 120b having a length "l" of 0.125". Spacer 164 can have a thickness "t" of 0.035" and a hole 170 having a dimension "d" of 0.200". As will be understood by one of ordinary skill having the benefits of this disclosure, this illustrative embodiment, for example, can penetrate the surface 168 being lanced up to 0.090" which is the difference between the exemplary length "l" of needle 120a and the exemplary thickness "t" of spacer 164. As another example, surface 168 can be penetrated up to 0.065" where spacer 164 has a thickness of 0.060" and needle 120b has a length of 0.125".

The thickness "t" of spacer 164 can be any thickness required by a particular application, wherein the greater the thickness "t", the lesser the lance penetration depth, and vice versa, for a particular length "l" of a needle 120a required by a particular application. The thickness "t" of a particular spacer 164 can advantageously allow at least a portion of needle 120b to penetrate surface 168, such as skin or another lancing surface, so that blood 176 may leave surface 168. Exemplary thicknesses of spacer 164 can include 0.100", 0.080", 0.060", 0.040", and 0.020", as well as thicknesses greater than, less than, or between such values. Spacer 164 can be calibrated for any surface, such as for one or more areas of a user's skin. For example, spacer 164 can be relatively thin for some surfaces, such as where blood vessels are scarce or more distant from the surface of the skin, or spacer 164 can be relatively thick for other surfaces, for example, where blood may be closer to the skin, which can vary from application to application, or from user to user. Bottom surface 174 of spacer 164 can, but need not, be in direct contact with a lancing surface, for example, for allowing hole 170 to sealingly engage the surface. In at least one embodiment, for example, depth controller 162 can include an annular rim (not shown), which may comprise a seal, coupled to bottom surface 174 and extending downwardly to engage a lancing surface, singularly or in combination with bottom surface 174.

Depth controller 162 can include interchangeable or modular units, which can include interchangeable spacers 164 for a particular depth controller 162 or, as another example, interchangeable depth controllers 162 for a particular system 100, wherein one or more depth controllers 162 can, but need not, have spacers 164 of different calibrated thicknesses. Each interchangeable unit can be graduated and can, for example, vary incrementally from unit to unit. In at least one embodiment, which is but one of many, system 100 can include a plurality of depth controllers 162, such as a set or kit, which can include a plurality of different depth controllers or spacers that can be selectively changed or switched by a user as required by a particular application. In at least one embodiment, which is but one of many, a set of depth controllers 162 may be stored, or storable, in a container, such as a bag or case, such as when not in use. A user can choose to use any of one or more depth controllers 162 required by a particular application, which can include choosing to use a depth controller already coupled to device body 102 or, as another example, can include choosing a depth controller separate from device body 102 and coupling the chosen depth controller to device body 102.

Figure 8A:
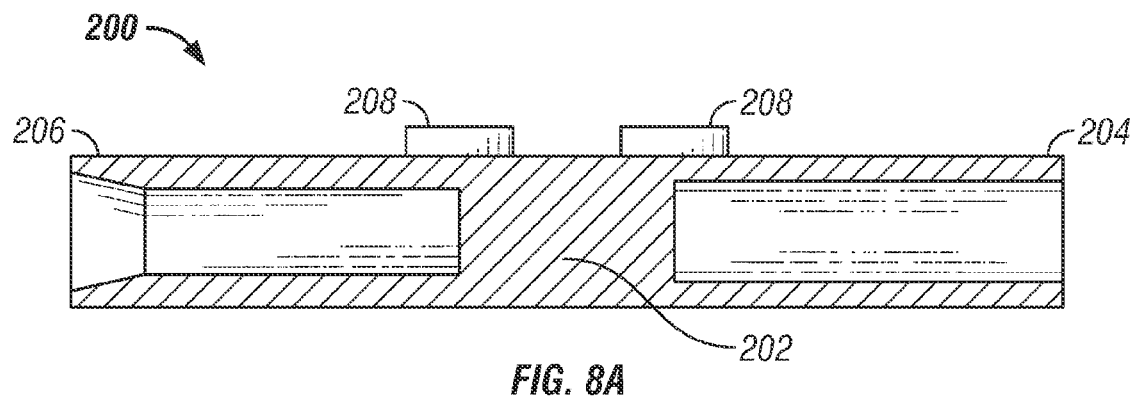
FIG. 8A is an illustration of one of many embodiments of a vacuum lance system having a lance tool according to the disclosure.
Figure 8B:
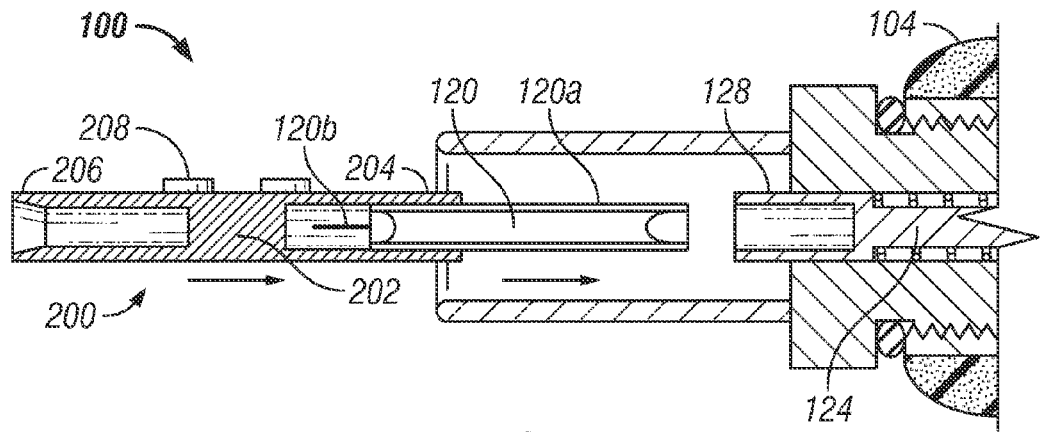
FIG. 8B is an illustration of a lance being inserted into a lance coupler with the lance tool of FIG. 8A.
Figure 8C:
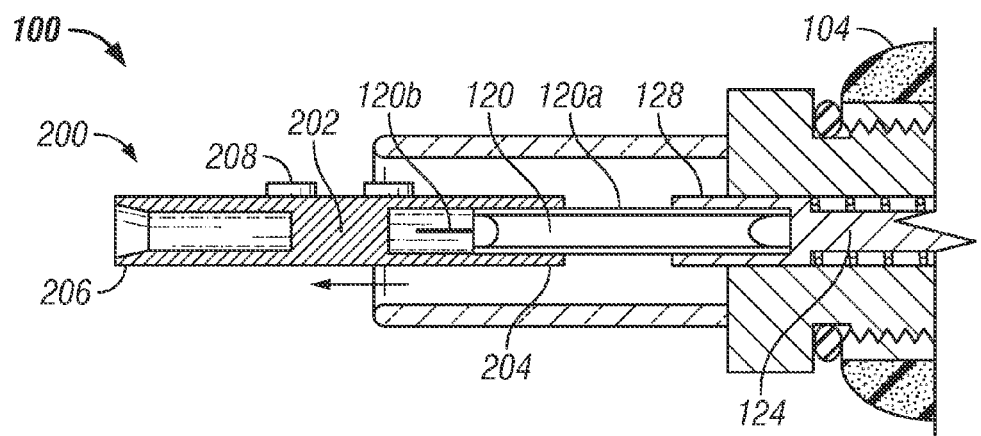
FIG. 8C is an illustration of a lance being coupled to the lance coupler with the lance tool of FIG. 8A.
Figure 8D:
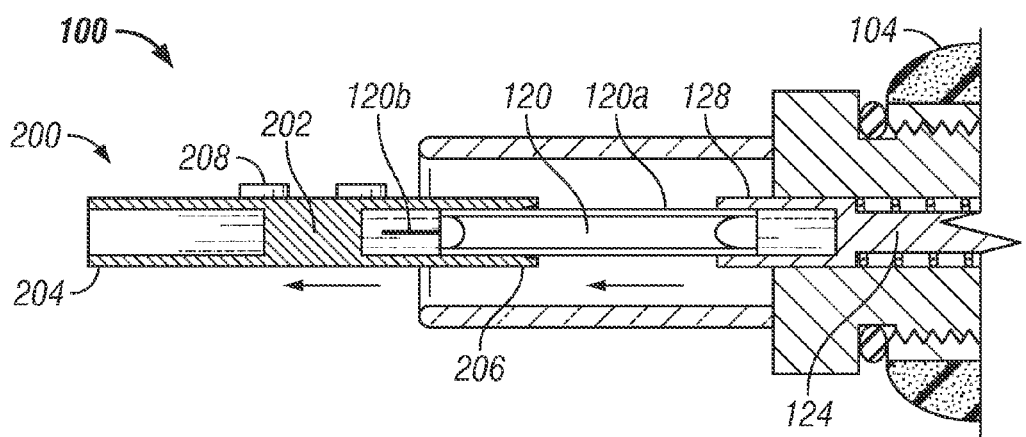
FIG. 8D is an illustration of a lance being removed from the lance coupler with the lance tool of FIG. 8A.

FIG. 8A is an illustration of one of many embodiments of a vacuum lance system having a lance tool 200 according to the disclosure. FIG. 8B is an illustration of a lance 120 being inserted into lance coupler 128 with lance tool 200. FIG. 8C is an illustration of a lance 120 being coupled to lance coupler 128 with lance tool 200. FIG. 8D is an illustration of a lance 120 being removed from lance coupler 128 with lance tool 200. FIGS. 8A-8D will be described in conjunction with one another. Vacuum lance system 100 can include a lance tool 200 for coupling and uncoupling a lance 120 with lance coupling end 124 of lancing shaft 122, such as to lance coupler 128, safely and conveniently. Lance tool 200 can include a lance tool body 202 and one or more couplers, such as, for example, lance insertion coupler 204 and lance removal coupler 206, which can, but need not, be tubular. For example, insertion coupler 204 and removal coupler 206 can, but need not, have annular cross-sections and/or one or more longitudinal slots to allow lance 120 to be inserted therein, as will be understood by one of ordinary skill.

To install lance 120 into system 100, for example, lance 120 can be inserted into insertion coupler 204 "needle end first" so that the needle 120b of lance 120 is inside insertion coupler 204 and so that base 120a of lance 120 couples with insertion coupler 204 and at least a portion of base 120a protrudes from insertion coupler 204 (see, e.g., FIG. 8B). In at least one embodiment, which is but one of many, base 120a and insertion coupler 204 can form a clearance fit or, as another example, an interference fit less than an interference fit between lance coupler 128 and base 120a. Insertion coupler 204 and lance 120 can be moved toward lancing end 104, as indicated by the arrows in FIG. 8B, and disposed so that the portion of base 120a protruding from insertion coupler 204 couples with lance coupling end 124 of lancing shaft 122, such as to lance coupler 128 (see, e.g., FIG. 8C). For example, as mentioned above, lance base 120a can form an interference fit with lance coupler 128 so that lance 120 uncouples from insertion coupler 204 and remains seated in lance coupler 128 for lancing when lance tool 200 is removed from lance guide 112, as indicated by the arrow in FIG. 8C.

To remove lance 120 from lance coupler 128, for example, lance removal coupler 206 can be inserted into lance guide 112 until removal coupler 206 passes over needle 120b and couples to base 120a of lance 120. For example, removal coupler 206 and base 120a can form an interference fit, such as an interference fit having a greater interference (i.e., a tighter fit) than the interference fit formed between base 120a and lance coupler 128. Lance tool 200 and lance 120 can be moved away from lance coupler 128, as indicated by the arrows in FIG. 8D, and lance 120 can uncouple from lance coupler 128 and remain coupled to removal coupler 206, which can remove lance 120 from lance coupling end 124.

Although lance insertion coupler 204 and lance removal coupler 206 of the lance tool 200 have been described herein to communicate with lance 120 using one or more "fits," such as an interference or clearance fit, this need not be the case, and, alternatively, each coupler 204, 206 can couple with lance 120 in any manner required by a particular application, as will be understood by one of ordinary skill in the art. As one example, which is but one of many, lance 120 can threadably couple to lance coupler 128, and one or more of couplers 204, 206 of the lance tool 200 can include a notch, groove, or other structure for communicating with lance 120, such as in a complementary fashion, separately or in combination with a particular fit, for example, for screwing lance 120 into or unscrewing lance 120 from lance coupler 128.

In at least one embodiment of lance system 100, which is but one of many, lance tool 200 can be coupled to lance device body 102, such as to the exterior along its length, when not in use. For example, lance device body 102 or lance tool 200 can, but need not, have at least one holder 208, such as complementary couplers, mounted thereon, such as, for example, magnets, hook and loop material, snaps or other fasteners. As other examples, device body 102 can have a hook, brace, grip or other holder coupled thereto and adapted to hold lance tool 200, such as by tool body 202, or device body 102 can have a stud or bracket adapted to couple to insertion coupler 204 or removal coupler 206. Lance tool 200 can be formed from any material required by a particular application, such as plastic, metal or another material, and can be any shape or size, as will be understood by one of ordinary skill in the art having the benefits of this disclosure.

FIG. 9 is a cross-sectional schematic view of one of many embodiments of a vacuum lance system 300 having an external vacuum indicator 302 according to the disclosure. For purposes of clarity, the same reference numerals as those used previously herein will be used in some instances, while new reference numerals will be used to reference components that may not have been described above. It should be understood that although the same reference numeral may be used to reference a component in two or more Figures, the component can, but need not, be exactly the same in practice, as required by a particular embodiment or application.

Lance system 300 can generally function similarly to one or more of the other embodiments described herein, and can include an external vacuum indicator 302 coupled to device body 102 for indicating whether a vacuum is present in the system. Indicator 302 can include an indicator body 304 coupled in fluid communication with vacuum chamber 154, such as with indicator air tube 306, which may be any type of conduit. Indicator 302 can include a marker 310 sealingly coupled inside indicator body 304 and an indicator spring 308 coupled between marker 310 and vacuum chamber 154. Indicator 302 can include a viewing window 312 for viewing marker 310, such as, for example, when no vacuum exists in the system. Window 312 can be coupled anywhere to indicator body 304, for example, to the top or side, and can be any size. For example, window 312 can, but need not, be at least a portion of indicator body 304 and can be at least partially transparent, such as a thin transparent strip along the length of indicator body 304. Alternatively, for example, indicator body 304 can be wholly transparent.

Indicator 302 can be coupled to device body 102 in any location between a surface being lanced and piston 148. Indicator 302 can be an "L-type" indicator (as shown in FIG. 9), for example, so that indicator body 304 is parallel to device body 102, a "T-type" indicator, for example, so that indicator body 304 is perpendicular to device body 102 or, as another example, indicator 302 can be disposed at another angle, which can be any angle, relative to central longitudinal axis X of the system.

As a vacuum is created in system 300 during lancing, marker 310, such as a disk or other indicator, can travel toward tube 306, and, for example, spring 308 can be compressed. Marker 310 can, but need not, become invisible. As the vacuum is released during lancing, marker 310 can move along tube 306 and spring 308 can expand, which can move at least a portion of marker 310 into view, such as being visible through window 312. While indicator spring 308 can be shown to be a compression spring in FIG. 9 for illustrative purposes, it need not be, and can alternatively be a tension spring, or both, separately or in combination, as will be understood by one of ordinary skill.

With further reference to FIG. 9, system 300 can include at least one opening between vacuum chamber 154 and an atmosphere surrounding the vacuum chamber, as described above (see, e.g., FIG. 5A). For example, and without limitation, the embodiment of FIG. 9, which is but one of many, can include three openings 156A, 156B and 156C (collectively "opening 156"), but this need not be the case and, alternatively, system 300 may include any number of openings 156, such as one, two, or more, or none, as required by a particular application. Each opening 156, such as one or more of openings 156A-C, can be in piston 148, device body 102, or another portion of system 300, separately or in combination. Like the embodiment of FIG. 9, any embodiment of the present invention, such as one or more of the other embodiments shown or described herein, may include any number of openings 156 disposed in any location required by a particular application, separately or in combination, as will be understood by one of ordinary skill having the benefits of the present disclosure. While one or more openings 156 in a particular embodiment can afford a linear vacuum dissipation rate (see, e.g., FIG. 5H), this need not be the case and, alternatively, a rate of vacuum dissipation can be non-linear, as required by a particular application.

FIG. 10 is a cross-sectional schematic view of one of many embodiments of a vacuum lance system 400 having an external vacuum assembly 402 according to the disclosure. System 400 can include a lancing assembly 404 for lancing a surface, which can be any lancing assembly required by a particular application. Lancing assembly 404 can, but need not, include a vacuum mechanism coupled with main device body 408, such as, for example, one or more of the embodiments described herein, partially, separately or in combination. System 400 can include a lance 120, such as a commercially available lance, and a vacuum chamber 406, which can, but need not, extend at least partially inside main device body 408. System 400 can include an external vacuum assembly 402 for at least partially creating a vacuum in vacuum chamber 406. Vacuum assembly 402 can, but need not, be a second, additional or supplementary source of vacuum in system 400, and can operate separately or in combination with one or more other components, such as vacuum components, lancing components, or other components of system 400.

Vacuum assembly 402 can include a vacuum body 410 for supporting one or more components of the system. Vacuum body 410 can be tubular and can have a vacuum end 412 and a longitudinally opposite end 414. Vacuum body 410 can, but need not, be coupled to main device body 408, rigidly, removably, or otherwise. Vacuum assembly 402 can include a shaft 416, which can be slideably coupled to end 414. Vacuum assembly 402 can include a release mechanism 418 coupled, for example, to end 414 of vacuum body 410, which can cooperate with shaft 416 to removably hold shaft 416 or one or more other components in one or more positions. Vacuum assembly 402 can include a piston 420, which can be in sealing engagement with vacuum body 410, such as with an inner surface 422, for example, for creating, increasing the level of, or dissipating a vacuum within vacuum chamber 406. Piston 420 can, but need not, include an opening (see, e.g., FIG. 5E) therein for allowing fluid communication between vacuum chamber 406 and an atmosphere surrounding vacuum chamber 406. Vacuum assembly 402 can include one or more springs, such as spring 424, for biasing piston 420 in one or more directions, for example, toward end 414 of vacuum body 410. Vacuum assembly 402 can be fluidicly coupled to vacuum chamber 406, for example, by conduit 426, which can be any conduit, such as a pipe, tube or other conduit, for routing fluid. Therefore, vacuum chamber 406 can include conduit 426 and at least a portion of vacuum body 410.

The embodiment shown in FIG. 10, which is but one of many, can generally operate or function similarly to one or more other embodiments described herein, such as to create or release a vacuum, in whole or in part, in vacuum chamber 406. For example, vacuum assembly 402 can create at least a portion of a vacuum in vacuum chamber 406 and lancing assembly 404 can lance a surface before, during, or after the vacuum exists. Vacuum assembly 402 can, but need not, create or dissipate a vacuum in portions, such as segments or stages, for example, by movement of piston 420 in one or more directions. Vacuum assembly 402 can cooperate with lancing assembly 404 to form a vacuum, in whole or in part, for example, in an embodiment, which is but one of many, wherein lancing assembly 404 includes a vacuum mechanism or can otherwise be able to create at least a portion of a vacuum independent of vacuum assembly 402. Penetration of a surface can occur at any time during lancing, such as at a predetermined time during vacuum creation, as required by a particular application.

Having described above one or more exemplary embodiments of the present invention, another one of many embodiments will now be described. For purposes of clarity, the same reference numerals as those used previously herein will be used in some instances, while new reference numerals will be used to reference components that may, but need not, differ from those described above, in whole or in part. It should be understood that although the same reference numeral may be used to reference a component in two or more of the Figures, the component can, but need not, be exactly the same in practice, as required by a particular embodiment or application, and reference numerals used herein are arbitrarily chosen for ease of explanation. One or more of the components and principles described above are also applicable to the following embodiments, and vice versa, regardless of whether like reference numerals are used, as will be readily understood by one of ordinary skill in the art. Certain details may not be repeated for purposes of brevity and the avoidance of unnecessary repetition, although such details can apply uniformly to all embodiments of the present invention.

Figure 11:
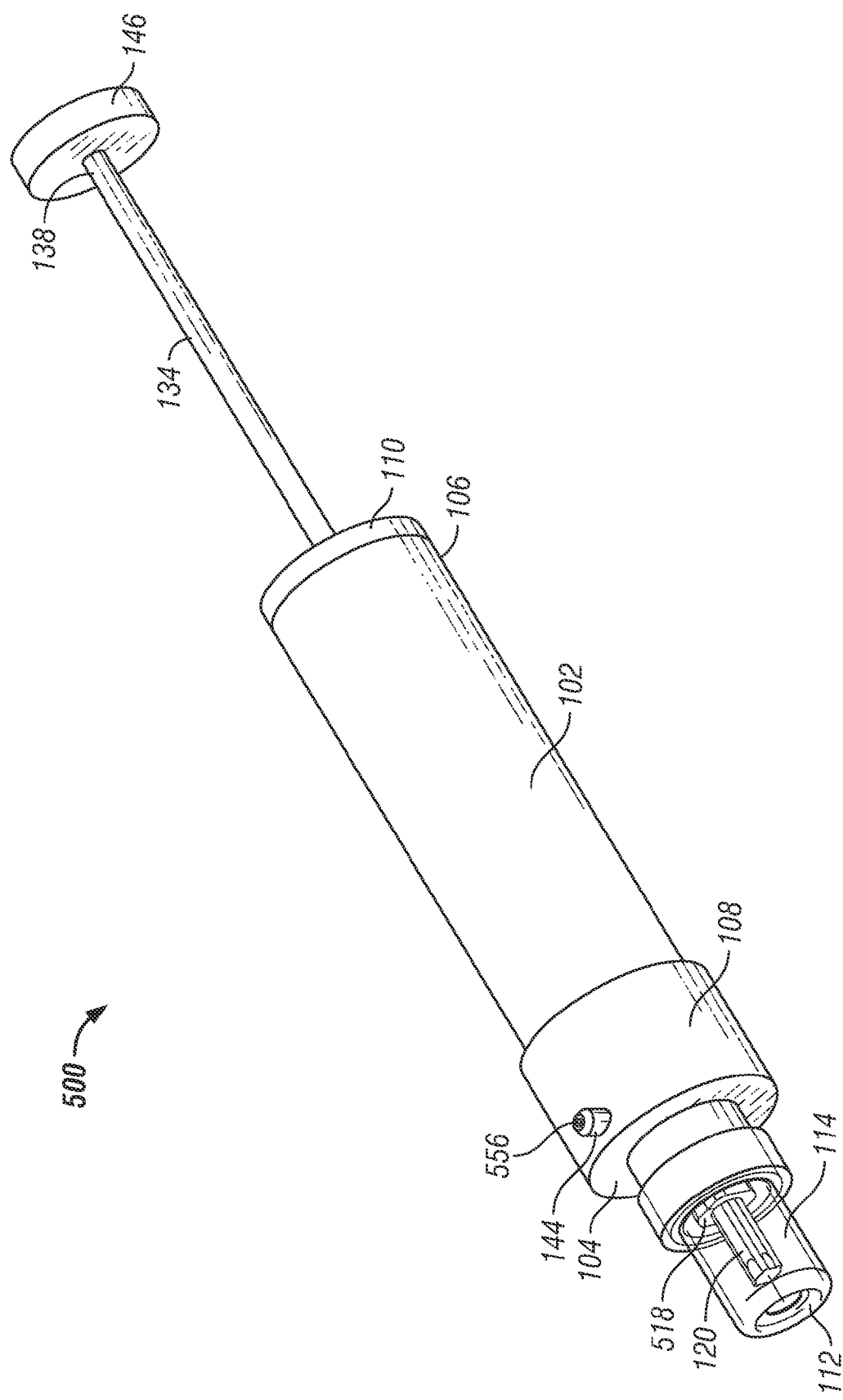
FIG. 11 is an isometric schematic view of another of many embodiments of a vacuum lance system according to the disclosure.
Figure 12:
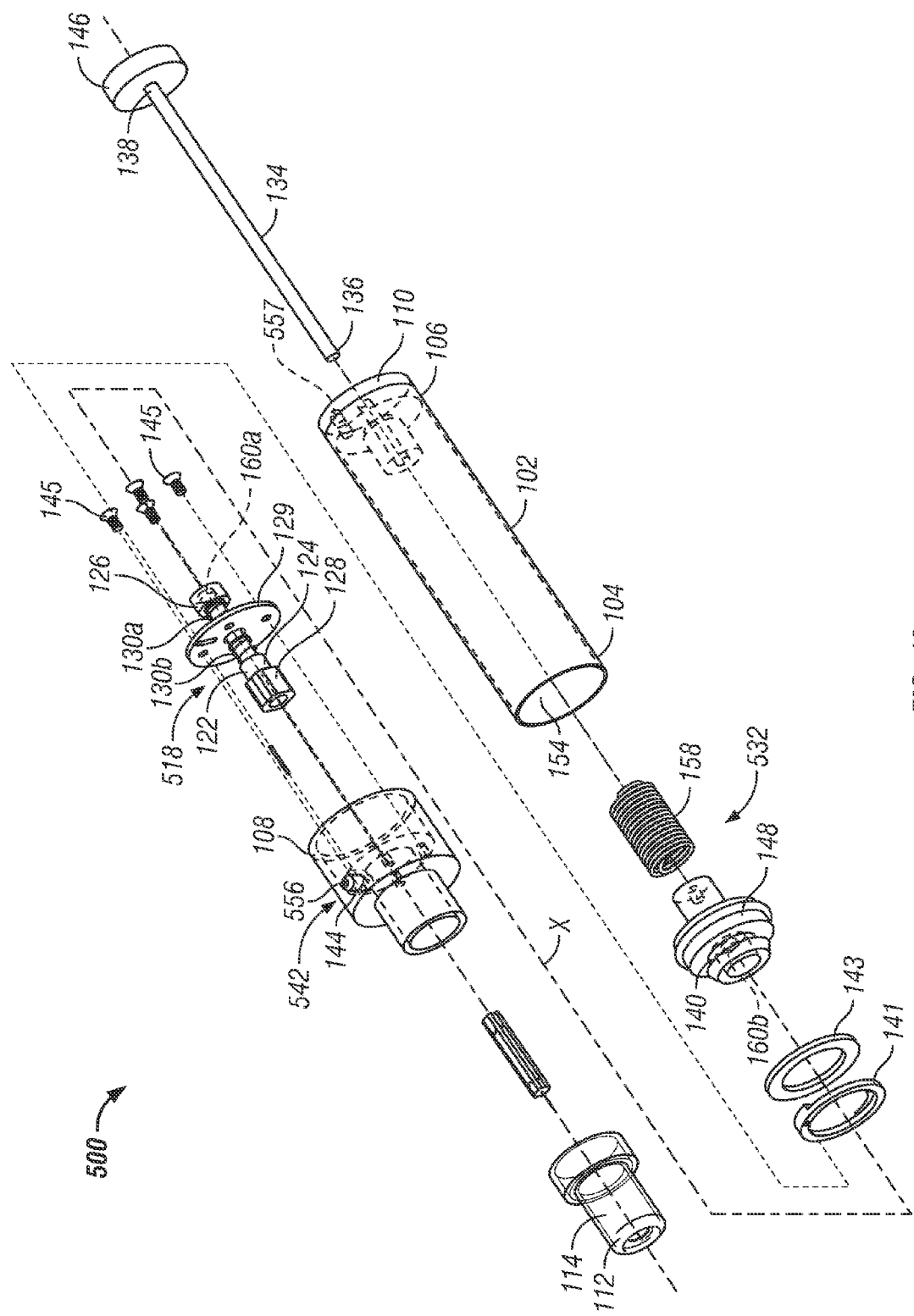
FIG. 12 is an isometric assembly schematic view of the vacuum lance system of FIG. 11.
Figure 13A:
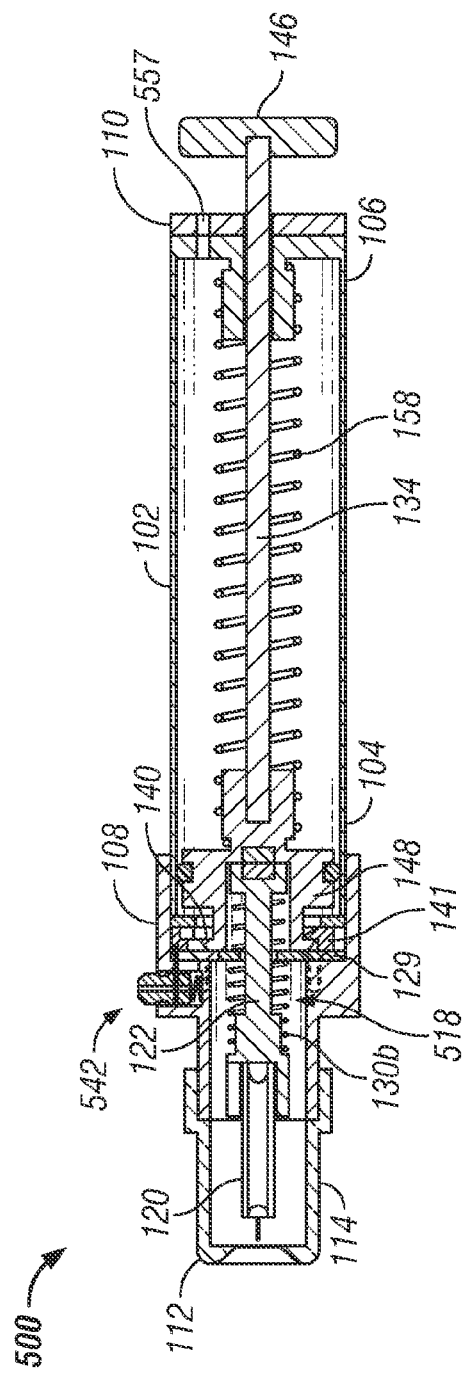
FIG. 13A is a cross-sectional schematic view of the vacuum lance system of FIG. 11 in a cocked position.
Figure 13B:
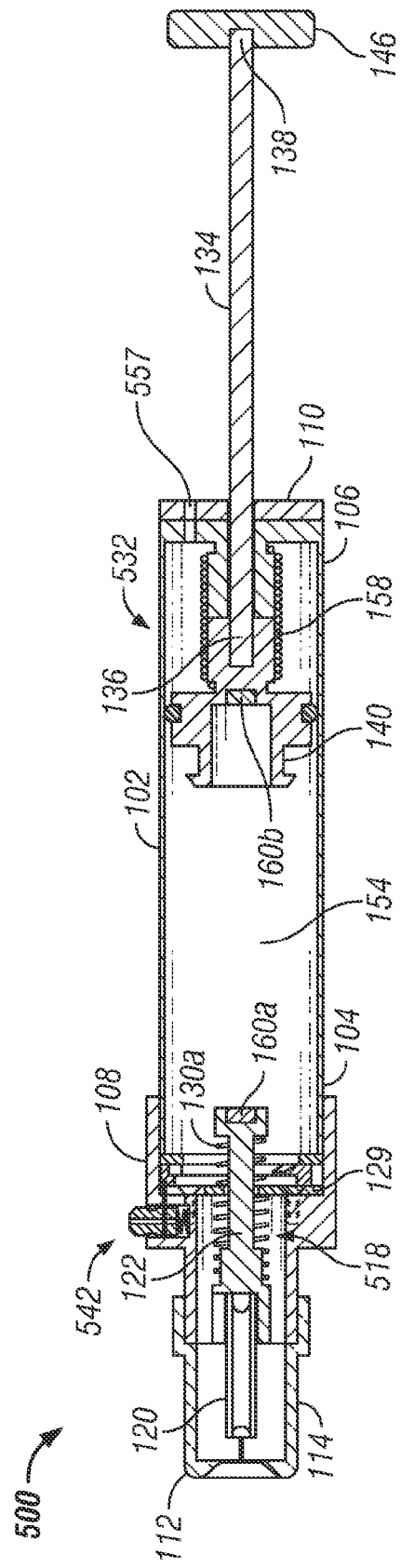
FIG. 13B is a cross-sectional schematic view of the vacuum lance system of FIG. 11 in an uncocked position.
Figure 14:
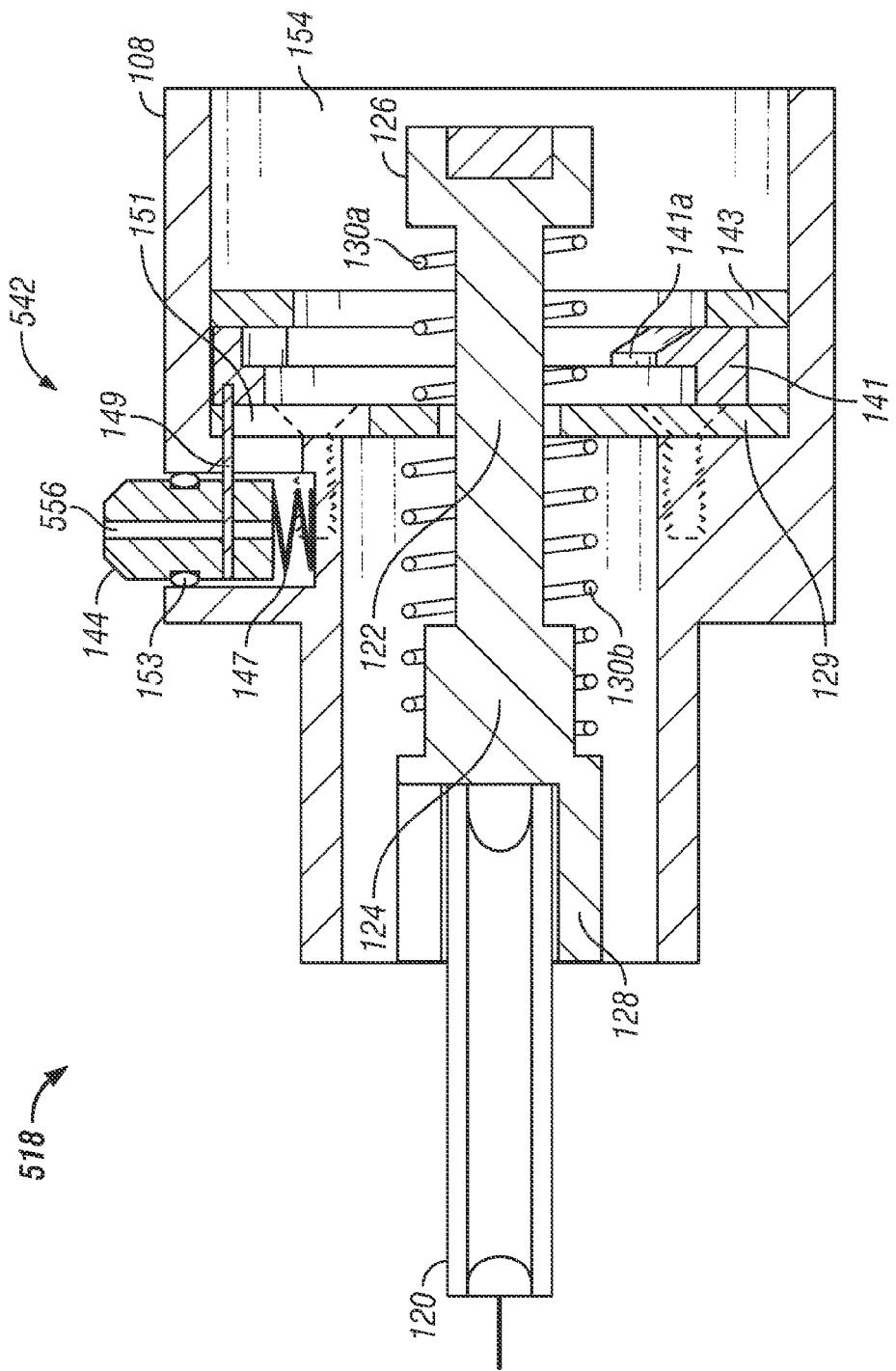
FIG. 14 is a cross-sectional schematic view of one of many embodiments of a lancing mechanism according to the disclosure.
Figure 14A:
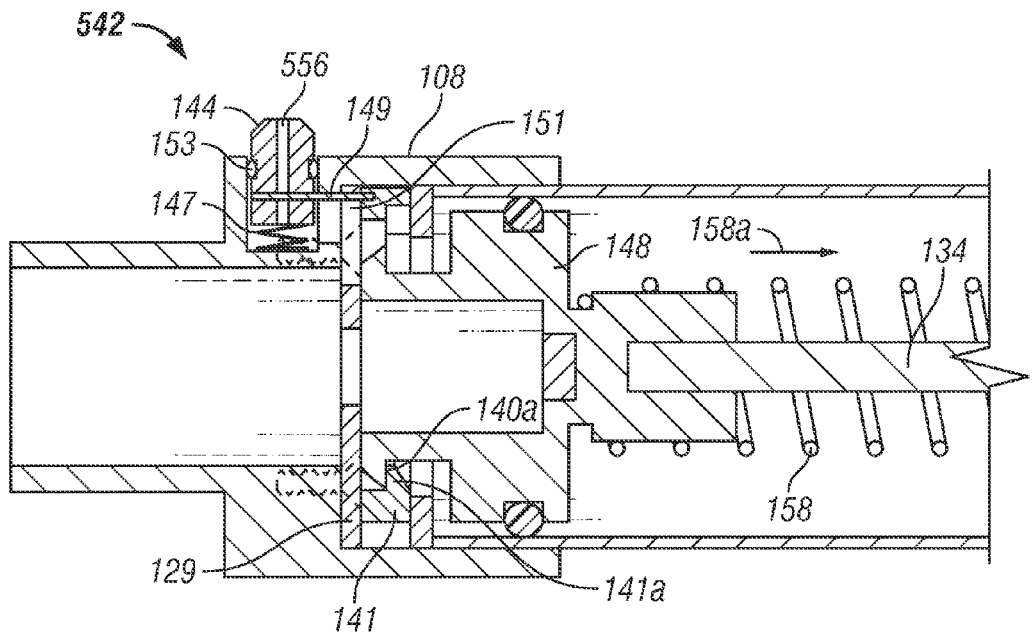
FIG. 14A is a cross-sectional schematic view of the release mechanism of FIG. 14 coupled to the main shaft before activation.
Figure 14B:
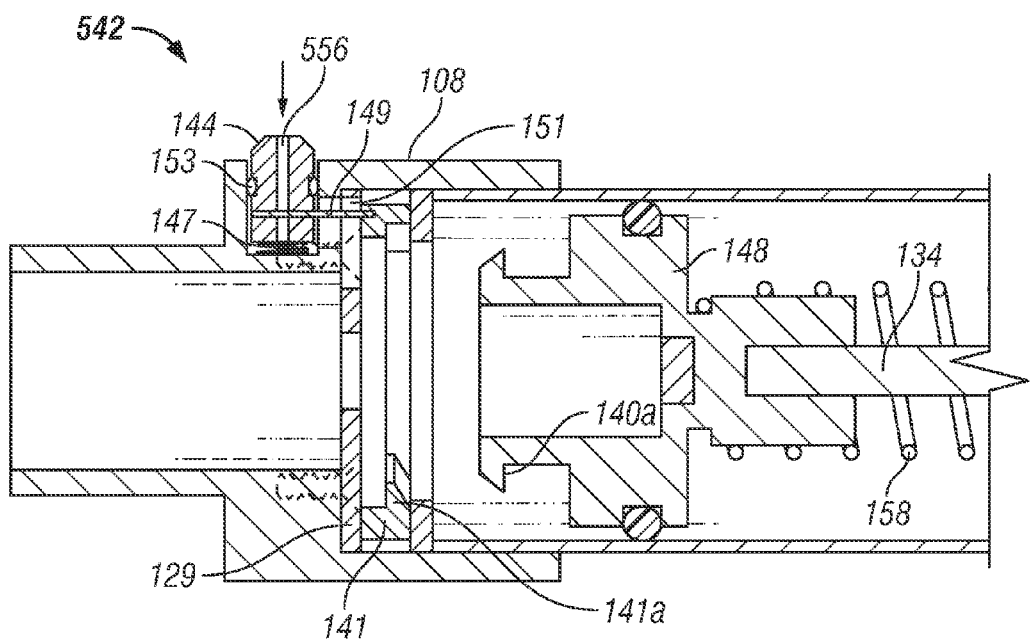
FIG. 14B is a cross-sectional schematic view of the release mechanism of FIG. 14A uncoupled from the main shaft after activation.
Figure 14C:
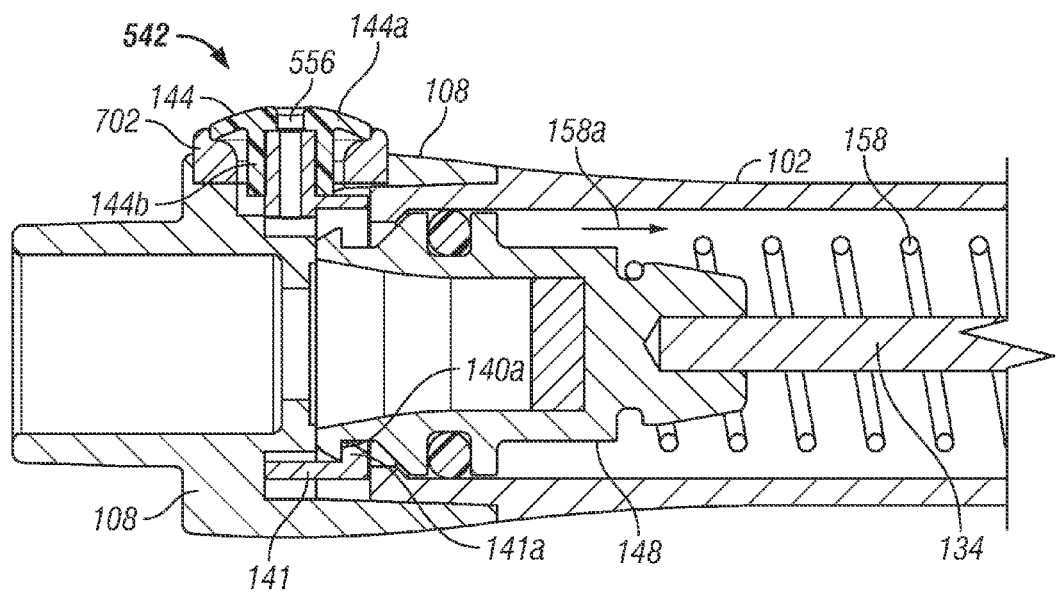
FIG. 14C is a schematic view of another of many embodiments of a release mechanism in a deactivated position according to the disclosure.
Figure 14D:
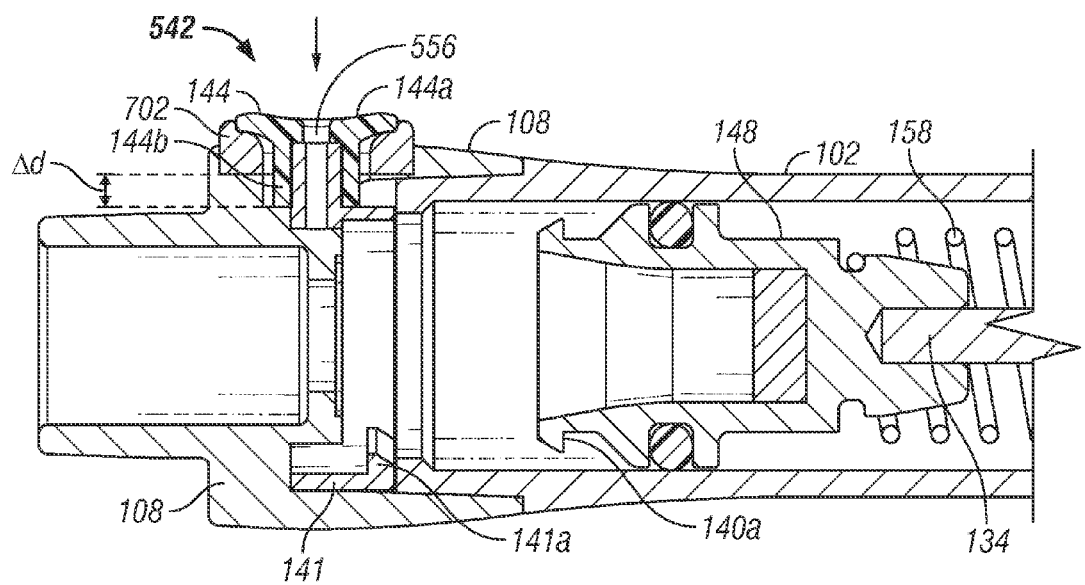
FIG. 14D is a schematic view of the release mechanism of FIG. 14C in an activated position according to the disclosure.
Figure 14E:
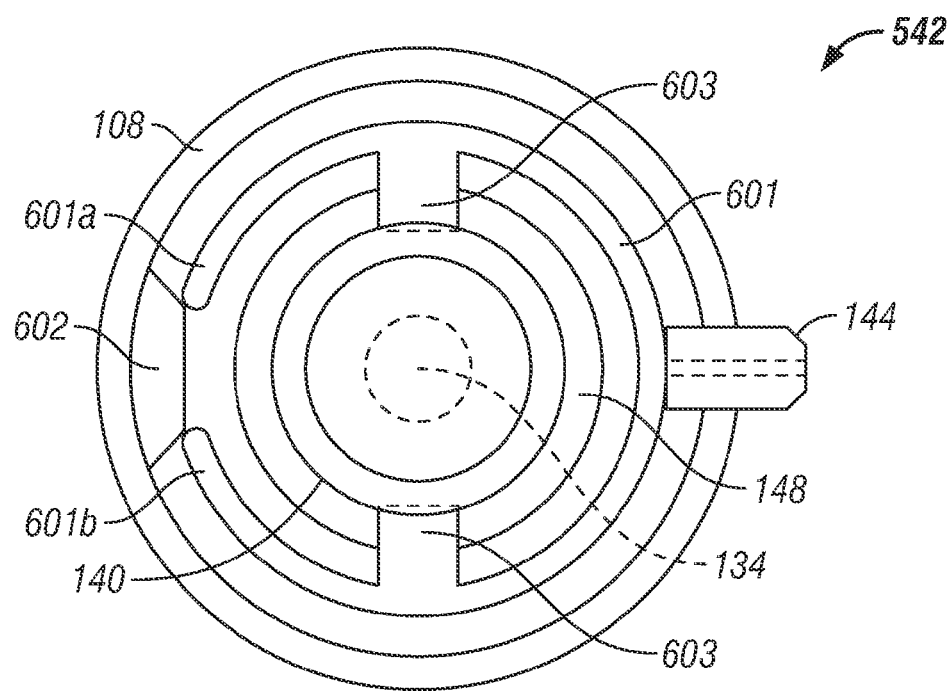
FIG. 14E is a schematic view of yet another of many embodiments of a release mechanism in a deactivated position according to the disclosure.
Figure 14F:
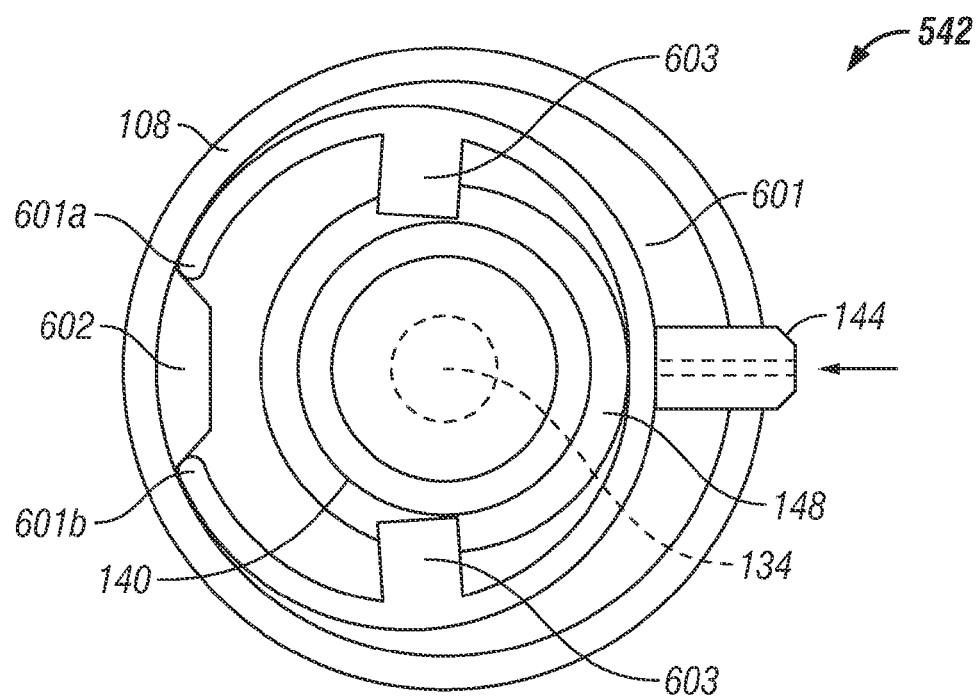
FIG. 14F is a schematic view of the release mechanism of FIG. 14E in an activated position according to the disclosure.

FIG. 11 is an isometric schematic view of another of many embodiments of a vacuum lance system according to the disclosure. FIG. 12 is an isometric assembly schematic view of the vacuum lance system of FIG. 11. FIG. 13A is a cross-sectional schematic view of the vacuum lance system of FIG. 11 in a cocked position. FIG. 13B is a cross-sectional schematic view of the vacuum lance system of FIG. 11 in an uncocked position. FIG. 14 is a cross-sectional schematic view of one of many embodiments of a lancing mechanism according to the disclosure. FIG. 14A is a cross-sectional schematic view of the release mechanism of FIG. 14 coupled to the main shaft before activation. FIG. 14B is a cross-sectional schematic view of the release mechanism of FIG. 14A uncoupled from the main shaft after activation. FIG. 14C is a schematic view of yet another of many embodiments of a release mechanism in a deactivated position according to the disclosure. FIG. 14D is a schematic view of the release mechanism of FIG. 14C in an activated position according to the disclosure. FIG. 14E is a schematic view of yet another of many embodiments of a release mechanism in a deactivated position according to the disclosure. FIG. 14F is a schematic view of the release mechanism of FIG. 14E in an activated position according to the disclosure. FIGS. 11-14F will be described in conjunction with one another.

Vacuum lance system 500 can include a device body 102, which can include one or more end caps 108, 110, coupled thereto or formed integrally therewith, in whole or in part. A lancing mechanism 518 can be coupled to body 102, such as to lancing end 104, for supporting a lance 120 (also known as a "lancet"). Lancing mechanism 518 can include a lancing shaft 122 slideably coupled with end cap 108, such as along central longitudinal axis X, for communicating lance 120 with a surface during lancing. Lancing shaft 122 can include a bottom lance coupling end 124 and a top actuating end 126. Lancing mechanism 518 can include a lance coupler 128 coupled to lance coupling end 124 for coupling lance 120 to shaft 122, removably or otherwise. Lancing mechanism 518 can include one or more biasing devices, such as a lancing spring 130. Lancing spring 130 can be coupled to lancing shaft 122 for biasing shaft 122 in one or more directions, temporarily, momentarily or otherwise, as will be further described below. Lancing spring 130 can, but need not, comprise a plurality of springs, and can advantageously include two springs.

System 500 can include a release mechanism 542, such as a firing assembly, which can include a release 144, one or more release couplers, and one or more components coupled there between, as further described below. Release mechanism 542 can include structure for cooperating with other components of system 500, such as lancing mechanism 518, vacuum mechanism 532, or other elements of the system, separately or in combination. Release mechanism 542 can be any type of releasable coupling system for lancing, and can be adapted to cooperate with main shaft 134, such as by optionally coupling with release coupler 140, piston 148, and/or other system components coupled to shaft 134, to releasably hold main shaft 134 in one or more positions. In at least one embodiment, release 144 can sealingly engage one or more portions of the system, such as body 102 or end cap 108, which can, but need not include one or more seals 153, such as an O-ring, gasket, or other device for at least partially limiting the entrance or escape of fluid, such as into or out of body 102 or vacuum chamber 154. At least three possible embodiments of release mechanism 542, which are but three of many, will now be described with reference to FIGS. 14-14F for illustrative purposes.

As one example, in the embodiment of FIGS. 14-14B, which is but one of many, release mechanism 542 can include a second release coupler 141, such as a catch or hook, for releasably coupling with coupler 140, such as a notch or groove (or vice versa) in any manner required by a particular application. The system can, but need not, include one or more retainers 143, such as a ring, washer, gasket, disk or other structure or fastener, for at least partially holding coupler 141 in place. Release mechanism 542 can include one or more biasing devices, such as spring 147, for biasing at least a portion of the mechanism, such as release 144 or coupler 141, in one or more directions, and can include one or more couplers or fasteners, such as pin 149, for coupling one or more mechanism components together. For example, pin 149 can couple release 144 and coupler 141 for translating motion therebetween. Pin 149 can pass through an opening 151 in stop 129, such as a slot, hole, or other opening. Spring 147 can bias release 144 toward a deactivated position, for example, radially outwardly, and can bias coupler 141, such as by biasing pin 149, toward a position for coupling with main shaft 134, such as with coupler 140. In a cocked position (e.g., FIG. 14A), couplers 140, 141 can be coupled and can hold piston 148 and main shaft 134 in a downward or other energized position. For example, catch 141a can be disposed adjacent to wall 140a for retaining piston 148 and main shaft 134, such as in a pre-firing position against the force 158a of vacuum spring 158.

With reference to FIG. 14B, release mechanism 542 can be activated by moving release 144 toward an activated position for allowing couplers 140, 141 to uncouple from one another. For example, by pressing release 144 radially inwardly (as illustrated by the vertical arrow in FIG. 14B), such as by sliding with a user's finger, or by another manner, including electronically, catch 141a can move from a cocked position adjacent to wall 140a to an activated position out of the way of coupler 140, which can allow couplers 140, 141 to uncouple. For example, catch 141a can be moved from a pre-firing position so that piston 148 and main shaft 134 are no longer retained against the force of vacuum spring 158, which can allow piston 148 and main shaft 134 to move toward an uncocked or deenergized position (e.g., to the right as illustrated by the horizontal arrow in FIG. 14B) as vacuum spring 158 compresses or deenergizes.

Turning to FIGS. 14C, 14D, as a second example, release 144 and coupler 141 alternatively can be formed integrally as a single component and pin 149 (FIG. 14A) can, but need not, be absent. In such an embodiment, which is but one of many, release 144 and coupler 141 can be made at least partially from elastic material, such as one or more elastomers (e.g., rubber) or shape-memory metals, separately or in combination, and spring 147 (FIG. 14A) can, but need not, be absent, as will be understood by one of ordinary skill in the art. For example, release 144 can be mushroom-shaped with its hat 144a adjacent the exterior of end cap 108, body 102, or a coupler 702 coupled thereto, such as a washer, grommet or seal, and its stem 144b extending radially inwardly toward release coupler 141. The elasticity of the material from which release 144, or one or more other system components, can be at least partially formed can allow a user to at least temporarily push or otherwise deform release 144 to activate system 500 (e.g., FIG. 14D), and can return the one or more pressed components, such as release 144 or other components, to a default position and can return the coupler 141 to a rest position (e.g., FIG. 14C) in a spring-like fashion. For example, as shown for exemplary purposes in FIG. 14C, release 144 can bias release coupler 141 in the upward direction (as illustrated) so that at least a portion of the coupler 141, such as catch 141a, interferes or otherwise couples with coupler 140, such as with wall 140a, for cocking the system. A user can apply a deforming or activating force or pressure (such as by applying a finger) to release 144, and the elastic resistance of release 144, which can be of any magnitude required by a particular application, can be at least partially overcome. Release 144 can force or push catch 141a some distance Δd, which can be any distance required by a particular application. Catch 141a can move out of a position of interference with wall 140a, which can allow piston 148 to move to the right (as illustrated) during firing of the system (FIG. 14D). Thus, as will be readily understood by one of ordinary skill in the art having the benefits of the present disclosure, the embodiment of FIGS. 14C, 14D operates similarly to that of FIGS. 14A, 14B, although the mechanics of one or more elastic components in the former can be substituted for those of one or more springs 147 in the latter, in whole or in part, separately or in combination.

A third example of a release mechanism, which is but one of many in accordance with the present disclosure, is shown in FIGS. 14E-14F. In at least one embodiment, release mechanism 542 can include a wishbone- or wedge-type mechanism for selectively holding piston 148 and main shaft 134 in a cocked position. For example, release mechanism 542 can include a U- or C-shaped coupler 601, such as a C-ring, circlip, snap ring or other coupler, and at least one wedge 602 for defining a path of movement of at least a portion of coupler 601, such as ends 601a, 601b. Wedge 602 can include any structure (or structures) that can cooperate with coupler 601 as described herein, such as one or more blocks or tapers. Coupler 601 can include one or more tabs 603, such as projections or other retainers, for coupling with one or more other components of the system, such as main shaft 134, piston 148 or release coupler 140. Coupler 601 can expand and contract against wedge 602, which can respectively increase and decrease a distance between tabs 603 for allowing tabs 603 to releasably couple and uncouple with shaft 134, such as by selectively retaining release coupler 140. In a cocked position (e.g., FIG. 14E), tabs 603 can be coupled with coupler 140, such as by being disposed adjacent thereto, and can hold piston 148 and main shaft 134 in a downward or other energized position, such as against the force 158a of vacuum spring 158. Release mechanism 542 can be activated by disposing coupler 601 in an activated position (e.g., FIG. 14F), for example, by pressing release 144 radially inwardly (as shown by the arrow in FIG. 14F for illustrative purposes), which can allow ends 601a, 601b to slide and spread against wedge 602, thereby at least partially separating tabs 603. Tabs 603 can uncouple from coupler 140, such as by moving radially outwardly from piston 148 or coupler 140, which can allow piston 148 and main shaft 134 to move toward an uncocked or deenergized position. Other types of release mechanisms can be coupled with system 500, separately or in combination with one or more of those specifically described herein, in whole or in part, as will be readily understood by one of ordinary skill having the benefits of the present disclosure. For example, although coupler 601 is shown in FIGS. 14E-14F for illustrative purposes to expand and contract against a wedge 602, coupler 601 could alternatively expand and contract between two or more opposing wedges or surfaces (not shown) to couple or uncouple with a corresponding release coupler 140, as will be readily understood by one of ordinary skill having the benefits of this disclosure.

System 500 can include a vacuum mechanism 532 for creating a vacuum and cooperating with lancing mechanism 518 or other components of the system during lancing. Vacuum mechanism 532 can include a main shaft 134 with a bottom main actuating end 136 and a top main free end 138, and at least one release coupler 140, which can, but need not, be coupled to piston 148. System 500 can, but need not, include a knob 146, such as a button or cap coupled to main free end 138. Vacuum mechanism 532 can include one or more pistons, such as piston 148, coupled to main shaft 134 for cooperating with one or more other components of system 500 to create a vacuum. Piston 148 can be coupled, adjustably, fixedly or otherwise, anywhere on main shaft 134 inside of device body 102, such as, for example, to main actuating end 136, and can at least partially form a vacuum chamber 154 inside device body 102. System 500 can include one or more openings 556, such as an air passage or orifice, for fluid communication between vacuum chamber 154 and an atmosphere surrounding the vacuum chamber. System 500 can include one or more openings between other portions of the interior of body 102 and the atmosphere, such as opening 557, for example, for allowing fluid (e.g., air) to flow in or out of body 102 as piston 148 moves along the body's length. Opening 557 can be disposed anywhere in the system, such as in free end 106 of the body, cap 110, or another location. Opening 556 can be calibrated to allow air to flow into vacuum chamber 154 at a predetermined vacuum dissipation rate, which can be any rate required by a particular application. Opening 556 can be any suitable place for fluidicly communicating with a vacuum in system 500, such as in device body 102, and can advantageously be, but need not be, in release 144. One or more openings 556 can afford any rate of vacuum dissipation required by a particular application, such as a linear rate, non-linear rate, or another rate, in whole or in part, separately or in combination.

Vacuum mechanism 532 can include a biasing device, such as vacuum spring 158, coupled to piston 148 for biasing piston 148 in one or more directions, such as in the upward direction toward free end 106. For example, vacuum spring 158 can include a tension spring, as shown in the embodiment of FIG. 12, which is but one of many, so that a rest position for release coupler 140 can be toward top end cap 110. System 500 can, but need not, include a vacuum indicator (such as one or more of the vacuum indicators described above; see, e.g., FIG. 2) for indicating whether or to what extent a vacuum exists within vacuum chamber 154. For example, in an application where skin is being lanced for purposes of drawing blood, it could at times be detrimental for the user to pull system 500 off the skin when there is still vacuum in chamber 154 because inrushing air could disperse or otherwise disrupt withdrawn blood pooled on the surface. For this reason, it can be advantageous for the user to know the vacuum level in chamber 154. A vacuum indicator can be calibrated to indicate when system 500 can be removed from the skin for at least minimizing any potential that drawn blood could splatter.

With further reference to FIGS. 12-14, system 500 can include a shaft coupler 160 for releasably coupling one or more components of the system, such as lancing shaft 122 and main shaft 134. For example, shaft coupler 160 can include a first portion 160a coupled to lancing shaft 122, such as to actuating end 126, and a second portion 160b coupled with main shaft 134, whether directly or indirectly, such as with piston 148. Lancing mechanism 518 can include a stop 129, such as a tab, block, disk or other structure, for supporting lancing spring 130 and defining a stroke of lancing shaft 122, in whole or in part. For example, upper spring 130a can be coupled between stop 129 and actuating end 126, and lower spring 130b can be coupled between stop 129 and lance coupling end 124. Stop 129 can be coupled with body 102, such as to end cap 108, in any manner required by a particular application, which may, but need not, include the use of one or more fasteners 145, such as screws, pins, adhesives, or other holding devices, separately or in combination. Alternatively, no fasteners 145 need be used, and stop 129 can be coupled with body 102 in another manner, such as by force or friction fit, or can be formed integrally with cap 108, in whole or in part.

Figure 15A:
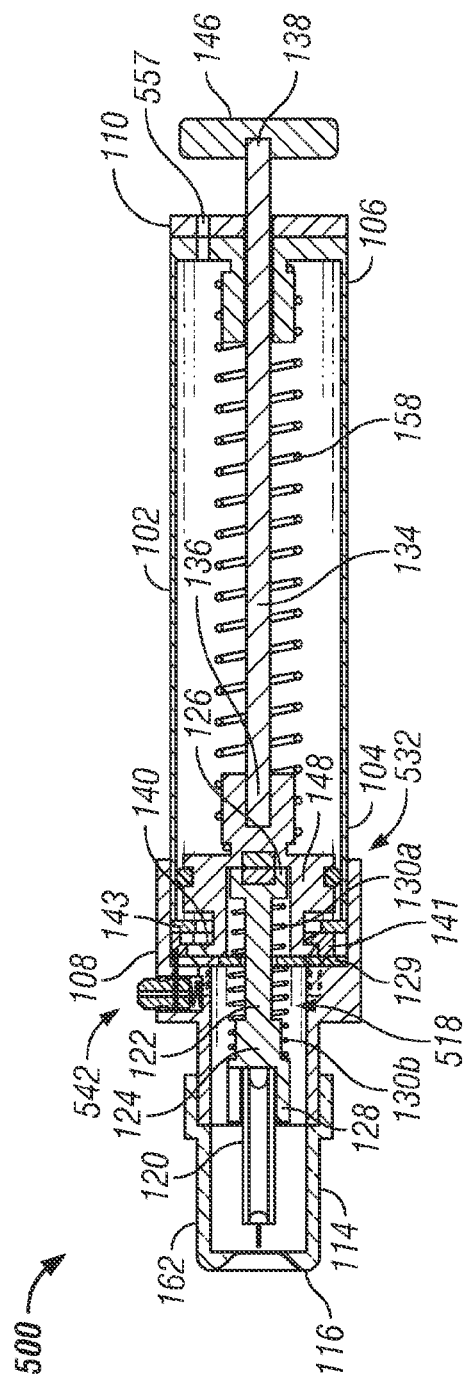
FIG. 15A is an illustration of the vacuum lance system of FIG. 11 in a cocked position according to the disclosure.
Figure 15B:
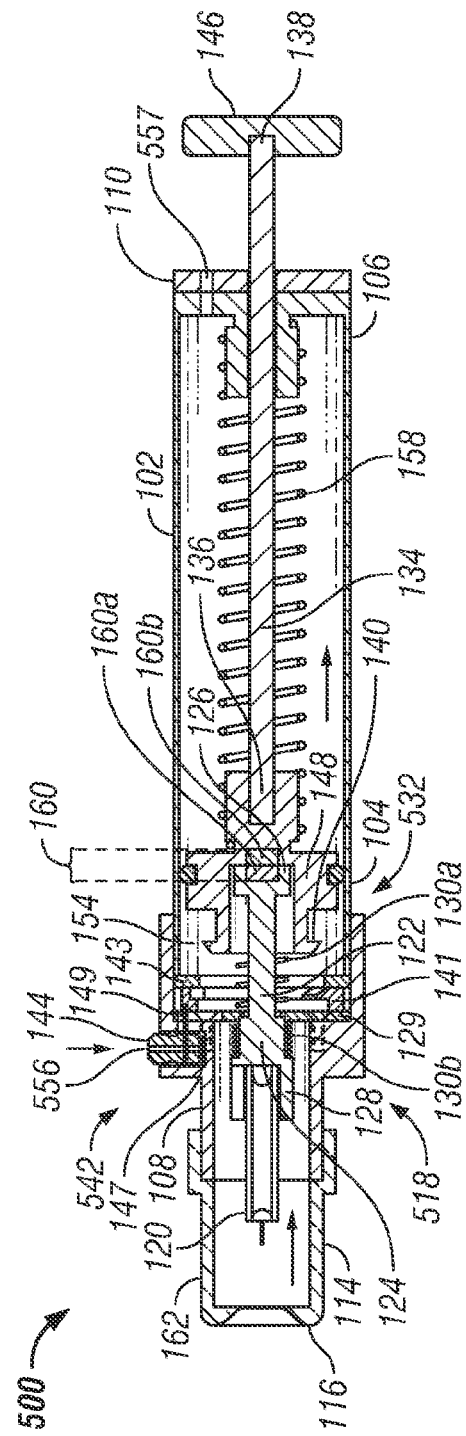
FIG. 15B is an illustration of the vacuum lance system of FIG. 15A in one of many activated positions wherein the first and second portions of the shaft coupler are coupled according to the disclosure.
Figure 15E:
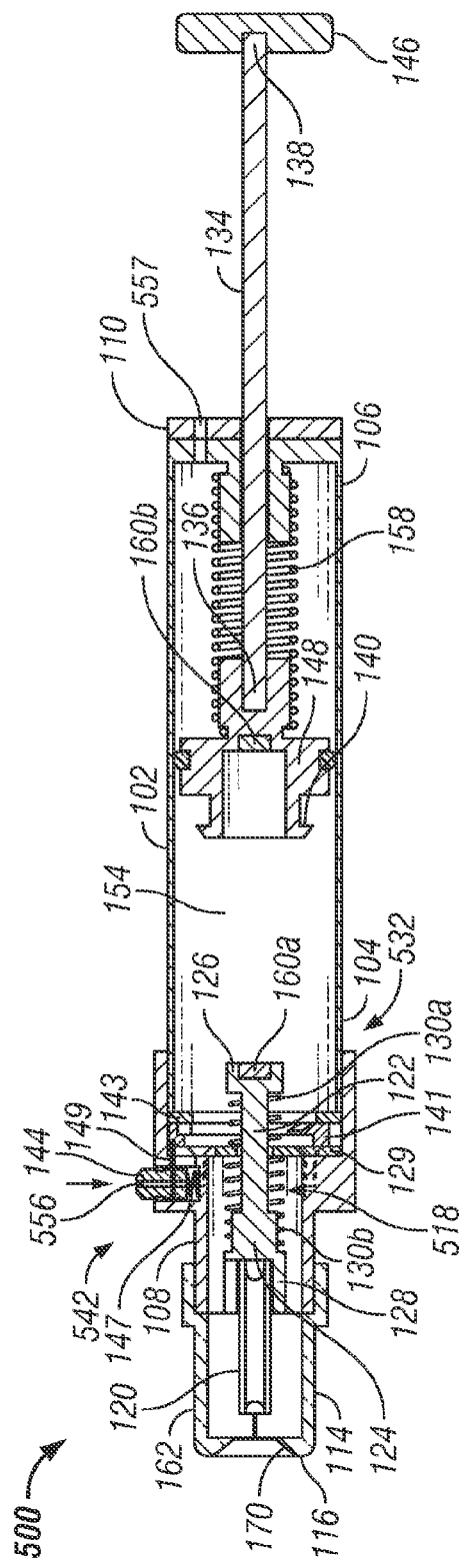
FIG. 15E is an illustration of the vacuum lance system of FIG. 15A in another of many activated positions wherein the opening in the release is not sealed according to the disclosure.
Figure 15F:
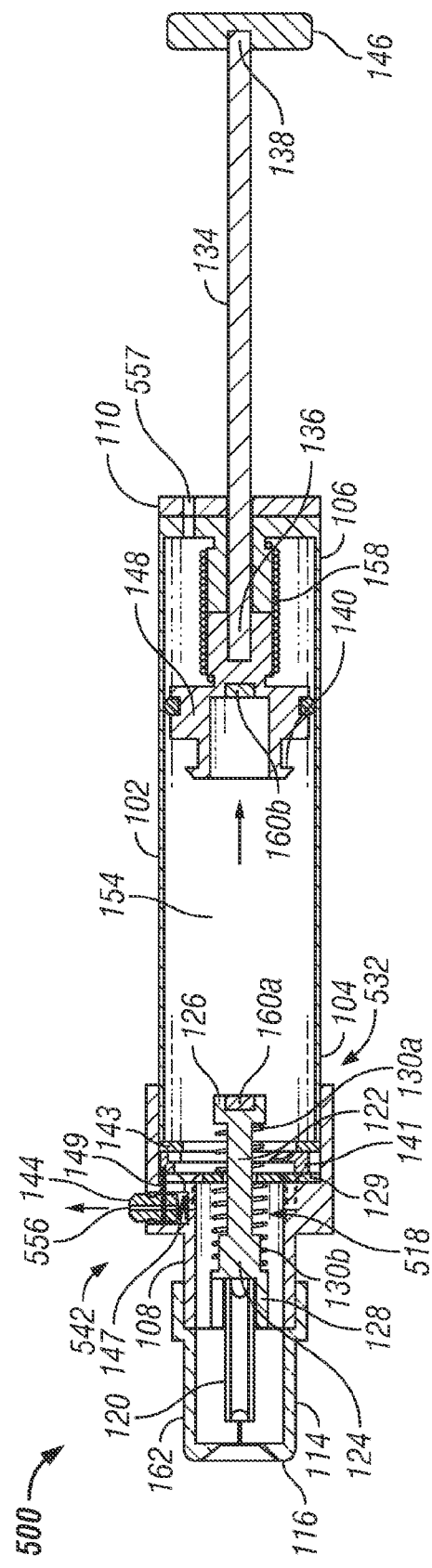
FIG. 15F is an illustration of the system of FIG. 15A in an uncocked position.
Figure 15G:
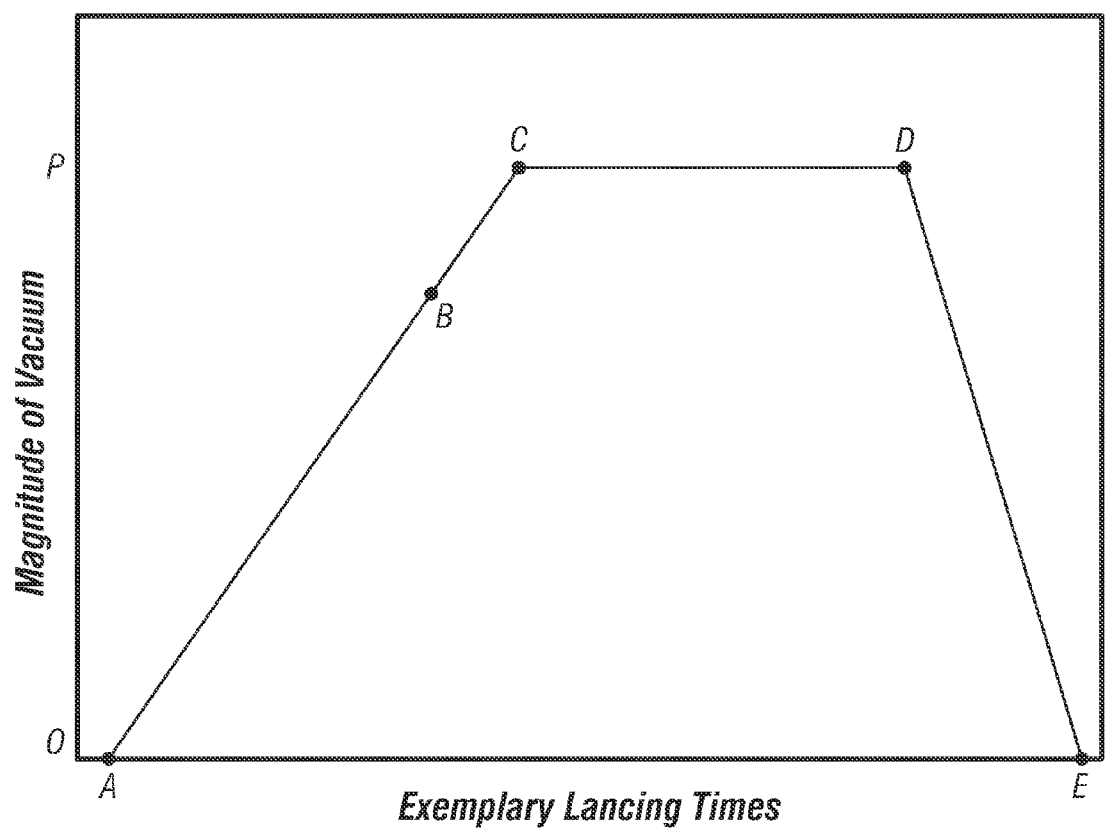
FIG. 15G is a graph illustrating another example of vacuum magnitude versus a time over which lancing can occur during a vacuum cycle according to the disclosure.

FIG. 15A is an illustration of the vacuum lance system of FIG. 11 in a cocked position according to the disclosure. FIG. 15B is an illustration of the vacuum lance system of FIG. 15A in one of many activated positions wherein the first and second portions of the shaft coupler are coupled according to the disclosure. FIG. 15C is an illustration of the vacuum lance system of FIG. 15A in another of many activated positions wherein the first and second portions of the shaft coupler are uncoupled according to the disclosure. FIG. 15D is an illustration of the vacuum lance system of FIG. 15A in another of many activated positions wherein the opening in the release is sealed according to the disclosure. FIG. 15E is an illustration of the vacuum lance system of FIG. 15A in another of many activated positions wherein the opening in the release is not sealed according to the disclosure. FIG. 15F is an illustration of the system of FIG. 15A in an uncocked position. At least one of many methods of using the embodiment of system 500 shown in FIGS. 15A-15F can be described. FIG. 15G is a graph illustrating another example of vacuum magnitude versus a time over which lancing can occur during a vacuum cycle according to the disclosure. FIGS. 15A-15G will be described in conjunction with one another.

A lance 120 can be coupled to lancing mechanism 518, such as by using one of the methods described herein, for example, before or after system 500 is in a "cocked" position (see, e.g., FIG. 15A). A lance guide, such as depth controller 162, can be coupled to lancing end 104, such as with end cap 108. System 500 can be cocked, for example, by pressing knob 146 downward until release coupler 140 couples with release mechanism 142, such as by releasably engaging coupler 141. First and second portions 160*a*, 160*b* of shaft coupler 160 can couple together to releasably couple the actuating ends of shafts 122, 134. Actuating end 126 can, but need not, move downwardly during cocking, temporarily or otherwise. Upper spring 130*a* and lower spring 130*b* can, but need not, be in their natural states. System 500 can contact a surface to be lanced (not shown), such as an area of skin on a person's body, which can be any area, and can advantageously form an at least partially airtight seal between depth controller 162, or a portion thereof, such as seal 116, and the surface. Seal 116 can be formed integrally with depth controller 162 (as shown for illustrative purposes) or can be a separate structure coupled to depth controller 162, separately or in combination.

A user can place his or her finger on release 144 in preparation for firing the system and opening 556 can advantageously be at least temporarily closed, for example, to at least substantially seal vacuum chamber 154 among body 102, piston 148 and the surface to be lanced. As shown in the embodiment of FIGS. 15A-15F, which is but one of many, opening 556 can advantageously be disposed through release 144, for example, so that a user can simultaneously block, plug or otherwise obstruct opening 556 upon engaging release 144 with a finger or other actuator (such as a glove or other object). However, this need not be the case, and, alternatively or collectively, opening 556 can be located elsewhere, such as through body 102 or cap 108, and a user may close the opening(s) in another manner, such as by using another finger. As another example, system 500 can include a valve (not shown), such as a ball valve, needle valve, or other device for regulating or directing fluid flow, for electively starting, stopping or otherwise controlling flow through one or more openings, such as opening 556.

As indicated by the arrows in FIGS. 15B-15C, system 500 can be activated by actuating (e.g., pressing inwardly) release 144, which can coupler 140 and coupler 141 to disengage or otherwise uncouple. Vacuum spring 158 can at least partially contract and piston 148, main shaft 134 and shaft coupler 160 can move in the upward direction away from the surface being lanced. Piston 148 can at least partially form a vacuum in vacuum chamber 154 as piston 148 moves away from the surface being lanced, and opening 556 can remain closed, for example, to sustain the sealed chamber. One or more components of lancing mechanism 118, such as actuating end 126 and lancing shaft 122 can move upward with main shaft 134, for example, due to the coupling force of shaft coupler 160 and the force of contracting vacuum spring 158. Upper spring 130*a* can expand and lower spring 130*b* can contract, which can, for example, singularly or in combination, exert an increasing force on first portion 160*a* of shaft coupler 160 in an opposite direction (e.g., downward) from a force exerted on second portion 160*b* by vacuum spring 158 (e.g., upward) as vacuum spring 158 contracts (FIG. 15B). Lancing shaft 122 can contact stop 129, which can limit a stroke of lancing shaft 122.

Shaft coupler 160 can uncouple and second portion 160*b* can continue moving in an upward direction (as illustrated in the FIGS. for illustrative purposes) while first portion 160*a* and lancing shaft 122 reverse and move in an opposite (e.g., downward) direction toward the surface to be lanced (FIG. 15C). Lance 120 can penetrate the surface and lancing mechanism 518 can return to a state of rest. Piston 148 can continue moving upwardly at least partially toward free end 106. As piston 148 moves toward free end 106, such as under the force of spring 158, a magnitude of vacuum formed in vacuum chamber 154 can gradually increase and opening 556 can remain closed (FIG. 15D). The vacuum can generate a force acting on piston 148 in a direction opposite a force of spring 158 (e.g., downwardly), and the magnitude of the vacuum force can eventually become greater than or equal to that of the spring force, for example, so that piston 148 can at least partially come to rest between its cocked and uncocked positions (FIG. 15E) along the length of body 102, which may occur anywhere along the length of the body or stoke of shaft 134 as required by a particular application.

At this point in the exemplary vacuum assisted lancing process, the magnitude of the vacuum can, but need not, be at least substantially constant, and the vacuum can act on the lanced surface, which can advantageously result in suction that at least partially draws, or helps draw, blood from the surface. The user can maintain the state of vacuum in vacuum chamber 154 by keeping opening 556 closed, for example, by keeping his or her finger sealingly disposed there against, which can, but need not, include holding release 144 at least partially in an actuated position (e.g., inwardly, as indicated by the arrow in FIG. 15E). The user can view the area in which the surface has been pierced, such as through viewing area 114, which can, but need not, be at least a portion of a lance guide (see, e.g., FIG. 1) or a depth controller 162, and can advantageously verify whether or when a desired amount of blood, such as enough blood for testing, has exited from the surface. Although the Applicant expects that a requisite or desired amount of blood will often be recognized by a user through experience in lancing and blood extraction, this need not be the case, and a volume of extracted blood can be quantified by other measures. For example, in at least one embodiment of the system, hole 170 can be sized or calibrated, such as through one or more dimensions, to contain a minimum volume of extracted blood required by a particular application.

In these manners, it will be apparent that a user can advantageously maintain the vacuum on the surface until a desired amount of blood is extracted, and, for example, can thereafter electively commence dissipation of the vacuum by opening or unblocking one or more openings 556, such as by removing his or her finger from release 144 and opening 556 (e.g., as indicated by the vertical arrow in FIG. 15F). Unblocking opening 556 can allow air to flow into vacuum chamber 154, and piston 148 can resume travel (e.g., as indicated by the horizontal arrow in FIG. 15F) toward free end 106 until, for example, vacuum mechanism 532 comes to rest in an uncocked position (FIG. 15F). The vacuum can be dissipated at any rate required by a particular application, and can advantageously be dissipated at a relatively rapid rate by unblocking the opening as soon as the user observes or verifies that a sufficient amount of blood, such as an amount adequate for testing, has been extracted. Such an advantage can at least partially minimize the amount of time over which the system contacts the skin while at the same time providing the user with a readily attainable indication that the elapsed time and vacuum magnitude have been sufficient for drawing a required amount of blood for the purpose of a particular application. At the user's option, such as can be determined from the user's visual feedback, system 500 can be disengaged from the surface, which can leave a quantity of blood in a pool on the surface for collection.

As explained above with reference to one or more other embodiments of the present invention, the surface can be subjected to a vacuum before, during, or after lancing, separately or in combination. Air can enter or leave vacuum chamber 154 and body 102 at any rate required by a particular application. A surface being lanced can, but need not, be manipulated during lancing, which can include twisting, pumping, pressing up and down, or any movement, separately or in combination (see, e.g., FIG. 5F). With continuing reference to FIGS. 15A-15F, and further reference to FIG. 15G, the timing and magnitude of vacuum creation and lancing can include one or more variables, as will be understood by one of ordinary skill, each of which can have any value required by a particular application. For example, the magnitude of the vacuum, the rate at which the vacuum can be created, the timing of lancing, such as when shaft coupler 160 uncouples, the rate at which lance 120 can travel, and the force with which lance 120 strikes a surface, or other factors, can be optimized for a particular application. Vacuum creation can occur in a single stage, or in multiple stages.

As shown for illustrative purposes in FIG. 15G, lancing of a surface can occur at any time before, during, or after a vacuum cycle, as may be suitable for a particular application. For example, lancing of the surface can occur before a vacuum is created, as indicated by reference A. Alternatively, lancing can occur while the vacuum is increasing in the device body, as indicated by reference B. As will be understood by one of ordinary skill having the benefits of this disclosure, reference B illustrates one of many lancing times during vacuum creation, and lancing can alternatively occur at any point along a line between references A and C. As another example, lancing can occur when the vacuum is at peak vacuum P, illustrated by reference C. In at least one embodiment of the present invention, such as, for example, the embodiment shown and described in FIGS. 15A-15F, the magnitude of vacuum, such as peak vacuum P, can be maintained for a period of vacuum holding time after lancing has occurred, as indicated by line CD. A holding time can be any period of time required by a particular application or otherwise chosen by a user, such as an amount of time sufficient to allow a desired amount of blood to exit the surface. A user can allow the vacuum to dissipate, in whole or in part, or can commence dissipation of the vacuum, at a timing of their choosing, for example, through manipulation of opening 556. Vacuum dissipation can occur at any rate required by a particular application, as indicated for illustrative purposes by the slope of line DE, such as until the vacuum has fully dissipated, as illustrated by reference E in FIG. 15G.

As described above, lancing can occur at any time during a vacuum cycle, including before, during, or after a vacuum is created, and can advantageously occur when at least a partial vacuum is created, such as between 30% and 70%, or any increment there between, of the maximum vacuum for a particular application. In at least one embodiment, which is but one of many, lancing can advantageously occur at between 40% and 60% of vacuum creation, or any increment there between, such as at 50% vacuum creation. For example, the maximum vacuum can be −20 in Hg, and the surface can be lanced when the vacuum in vacuum chamber 154 is, for example, −10 in Hg. However, this need not be the case, and the examples described herein are for illustrative purposes. The timing of lancing can, but need not, be adjustable. For example, in at least one embodiment, such as a commercial embodiment, which is but one of many, system 500 can include a plurality of interchangeable lancing shafts, each of which can have a different length, which can determine when lancing occurs during a vacuum cycle, as described above.

Figure 16:
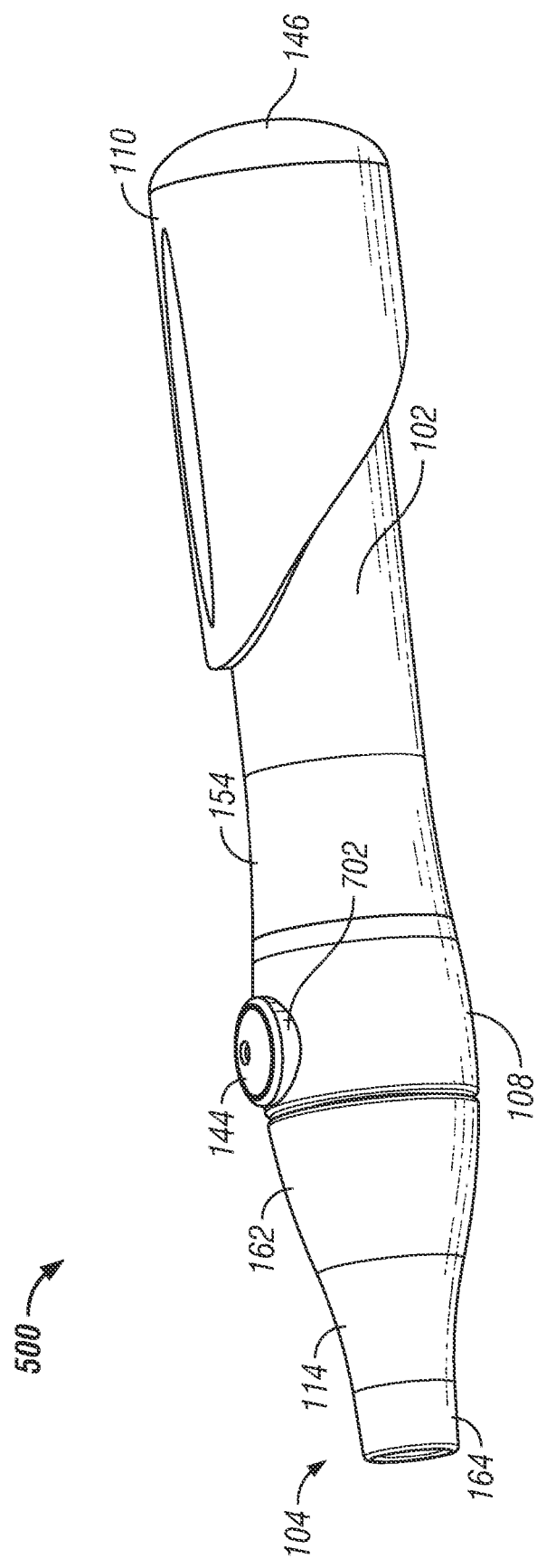
FIG. 16 is an isometric schematic view of yet another of many embodiments of a vacuum lance system according to the disclosure.
Figure 17:
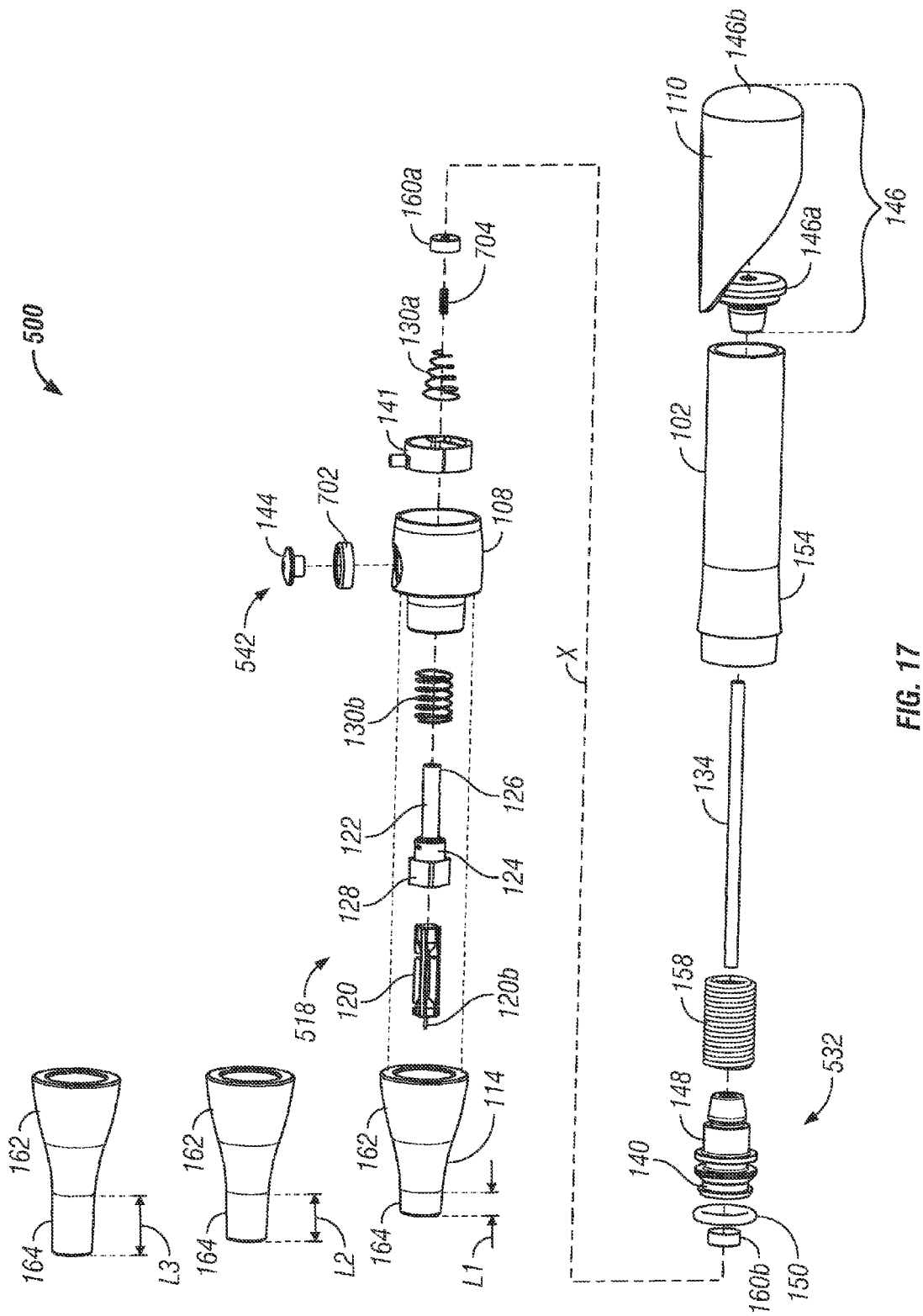
FIG. 17 is an isometric assembly schematic view of the vacuum lance system of FIG. 16.

FIG. 16 is an isometric schematic view of yet another of many embodiments of a vacuum lance system 500 according to the disclosure. FIG. 17 is an isometric assembly schematic view of the vacuum lance system 500 of FIG. 16. FIGS. 16-17 will be described in conjunction with one another. FIGS. 16-17 illustrate yet another of many embodiments of system 500, which can include a lancing mechanism 518, vacuum mechanism 532, and release mechanism 542, such as one or more of those described herein, separately or in combination, in whole or in part. This embodiment can generally function similarly to one or more of the other system embodiments described herein, as will be understood by a person of ordinary skill in the art having the benefits of the present disclosure, and like features and methods may not be described again here in order to avoid repetition.

As with one or more of the other embodiments shown and described in the present disclosure, the vacuum lance system 500 of FIGS. 16-17 can include a device body 102, which can include one or more end caps 108, 110, coupled thereto or formed integrally therewith, in whole or in part. Body 102 can, but need not, be at least partially curved or contoured, such as on its exterior, for providing a comfortable, ergonomic, or user-friendly grip as required by a particular application. A lancing mechanism 518 can be coupled to body 102, such as to lancing end 104, for supporting a lance 120 (also known as a "lancet"). Lancing mechanism 518 can include a lancing shaft 122 slideably coupled with end cap 108, such as along central longitudinal axis X, for communicating lance 120 with a surface during lancing. Lancing shaft 122 can include a bottom lance coupling end 124 and a top actuating end 126. Lancing mechanism 518 can include a lance coupler 128 coupled to lance coupling end 124 for coupling lance 120 to shaft 122, removably or otherwise. Lancing mechanism 518 can include one or more biasing devices, such as lancing springs 130a, 130b (collectively referred to as lancing spring 130). Lancing spring 130 can be coupled to lancing shaft 122 for biasing shaft 122 in one or more directions, temporarily, momentarily or otherwise, as further described above.

System 500 can include a release mechanism 542, such as a firing assembly, which can include a release 144, one or more release couplers, and one or more components coupled there between. As shown for exemplary purposes in FIGS. 16-17, system 500 can advantageously include the embodiment of release mechanism 542 shown in FIGS. 14C, 14D and described above, separately or in combination with one or more of the other exemplary release mechanisms described herein, in whole or in part. Release mechanism 542 can include structure for cooperating with other components of system 500, such as lancing mechanism 518, vacuum mechanism 532, or other elements of the system, separately or in combination. For example, release mechanism 542 can be adapted to cooperate with main shaft 134, such as by including one or more release couplers 141, for example, to optionally couple with release coupler 140, piston 148, and/or other system components coupled to shaft 134, to releasably hold main shaft 134 in one or more positions. In at least one embodiment, release 144 can sealingly engage one or more portions of the system, such as body 102 or end cap 108, which can, but need not include one or more couplers 702, such as an O-ring, gasket, washer, seal or other device for at least partially limiting the entrance or escape of fluid, such as into or out of body 102 or vacuum chamber 154. System 500 can include one or more shaft couplers, which can include one or more portions, such as first portion 160a and second portion 160b, for at least temporarily coupling together lancing shaft 122 and main shaft 134. Shaft coupler 160, or a portion thereof, can be coupled to another component of the system, such as one of shafts, 122, 134, in any manner required by a particular application, which can, but need not, include use of one or more fasteners 704, such as a pin, screw, bolt, shaft, adhesive, or other fastener, separately or in combination. System 500 can include a knob 146 for cocking the system, which can, but need not, include two or more portions coupled to one another, such as first portion 146a, second portion 146b and top end cap 110 (collectively referred to as knob 146). As is also shown and described above (see, e.g., FIGS. 11-14D), vacuum mechanism 532 can include one or more components for creating a vacuum in chamber 154, such as one or more vacuum springs 158 and pistons 148, which can, but need not, include one or more O-rings 150.

With continuing reference to FIGS. 16-17, system 500 can include one or more depth controllers 162, which advantageously can be at least partially formed from transparent material, for example, to include a viewing area 114, in whole or in part. Depth controller 162 can include interchangeable or modular units, which can include interchangeable spacers 164 for a particular depth controller 162. As another example, system 500 can include a plurality of interchangeable depth controllers, such as, for example, depth controller 162 and one, two, three or more alternative depth controllers 162. In either case, each interchangeable spacer 164 can, but need not, have a different calibrated length, such as lengths L1, L2 and L3, which can include any length required by a particular application. As another example, depth controller 162 can be adjustable, such as by way of one or more variable components, for example, a spacer 164 of varying length or thickness, as will be further described below. Typically, although not necessarily, the length of each spacer 164 can be less than the length of a particular lance needle 120b to be used with the spacer. Each interchangeable unit can be graduated and can, for example, vary incrementally from unit to unit. In at least one embodiment, such as a commercial embodiment, system 500 can include and be sold with a plurality of depth controllers as a set or kit. A user can choose to use any of one or more depth controllers 162 required by a particular application, which can include choosing to use a depth controller already coupled to device body 102 or, as another example, can include choosing a depth controller separate from device body 102 and coupling the chosen depth controller to device body 102. Similarly, system 500, or any set or kit including one or more components of system 500, can include a plurality of interchangeable biasing devices, such as one or more interchangeable lancing springs 130a, 130b or vacuum springs 158 for altering one or more lancing characteristics of the system. For example, each interchangeable biasing device can have one or more unique characteristics, such as dimensional, material, or elasticity characteristics (e.g., spring constant). A particular biasing device, or combination of biasing devices, can be chosen and implemented as required by a particular application based on one or more application-specific factors, such as the material or surface to be lanced, the depth of lancing, required lancing or vacuum forces, or other factors, as will be readily understood by one of ordinary skill having the benefits of Applicant's disclosure.

Figure 18:
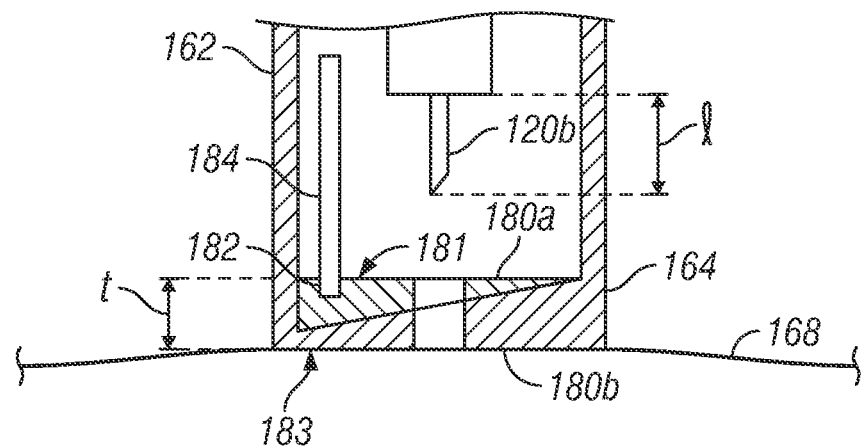
FIG. 18 is a schematic view of one of many embodiments of a vacuum lance system having an adjustable depth controller in a first position according to the disclosure.
Figure 19:
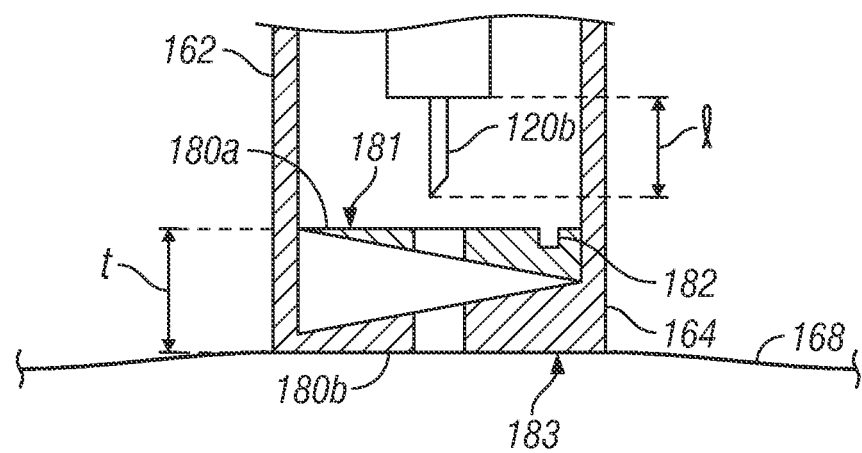
FIG. 19 is a schematic view of the system of FIG. 18 with the adjustable depth controller in a second position.

FIG. 18 is a schematic view of one of many embodiments of a vacuum lance system 500 having an adjustable depth controller 162 in a first position according to the disclosure. FIG. 19 is a schematic view of the system 500 of FIG. 18 with the adjustable depth controller 162 in a second position. FIGS. 18 and 19 will be described in conjunction with one another. As described above, vacuum lance system 500 can include one or more depth controllers 162 for controlling the depth of lancing, which can include one or more spacers 164 that can be interchanged, such as individually or by way of interchangeable depth controllers 162 (see, e.g., FIG. 17). The general structure and function of one or more depth controllers 162 in accordance with the present invention have been described above, for example, with respect to FIGS. 6-7C, and need not be fully repeated. Turning to yet another of many embodiments of depth controller 162, system 500 can include an adjustable depth controller 162 for controlling the depth of lance penetration, which can, but need not, take the place of one or more of a plurality of interchangeable depth controllers or spacers, and which can alternatively be used in conjunction therewith, in whole or in part. As shown in FIGS. 18-19, depth controller 162 can include adjustable structure, which can be any structure required by a particular application, for varying the thickness "t" of spacer 164 over a range of values, such as between a thickness for minimum penetration of surface 168 by lance needle 120b, including no penetration, and a thickness for maximum penetration of surface 168. As described above, base 120a can contact an upper surface of spacer 164 during lancing, which can limit the depth to which needle 120b can penetrate surface 168, such as to the difference between length "l" of needle 120b and the thickness "t" of spacer 164. As will be understood by one of ordinary skill in the art having the benefits of Applicant's disclosure, the value of thickness "t" can be maximized in order to minimize, or even prevent, the depth of lance penetration, and the value of thickness "t" can be minimized in order to maximize the depth of lance penetration. For example, depth controller 162 can have a "safety" setting wherein the value of thickness "t" can be greater than or equal to the value of length "l" of needle 120b, thereby preventing needle 120b from protruding beyond spacer 164 when not intended, such as during storage, travel or periods of non-use.

With continuing reference to FIGS. 18-19, one of many embodiments of an adjustable depth controller 162 can include an adjustable spacer 164 for varying thickness "t". For example, spacer 164 can include one or more blocks 180a, 180b (collectively referred to herein as blocks 180), such as shims, wedges, disks, or other structure, for at least temporarily defining the adjustable thickness "t" of spacer 164. For example, at least one of the blocks, such as topmost block 180a, can be moveable, for example by rotating, sliding or other motion, separately or in combination, to change the relative positions of the blocks, thereby increasing or decreasing the overall thickness "t" of spacer 164, such as by changing the distance between surfaces 181, 183 of the blocks. Alternatively, both blocks 180 can, but need not, be moveable. Blocks 180 can, but need not, be coupled to one another, and a moveable block can cooperate with depth controller 162 in any manner required by a particular application, for example, by translating along a groove or other path, by friction fit or by rotating about or along a guide structure, separately or in combination. In at least one embodiment of a lancing system having an adjustable depth controller 162, which is but one of many, one or more blocks 180 can have a coupler 182 for manipulating the one or more blocks to adjust the thickness of spacer 164. Coupler 182 can be any type of coupler required by a particular application, such as an opening, a protrusion, a threaded, grooved, notched or otherwise keyed hole (partial or thru), or other structure. Alternatively, coupler 182 can be absent. Coupler 182 can, but need not, be adapted to couple or otherwise cooperate with one or more actuators 184 for moving one or more blocks 180 between one or more positions to at least temporarily define or "set" the thickness of spacer 164. Actuator 184 can be any type of actuator required by a particular application, such as a rod, lever or other structure, and can be coupled to coupler 182 temporarily, permanently, or otherwise, including being formed integrally therewith, in whole or in part. As another example, actuator 184 can be a user-supplied actuator, such as a user's fingertip or another device for moving a block 180, for example, a bobby pin, toothpick, the head of a pen or pencil, or another device. As will be readily understood by one of ordinary skill having the benefits of Applicant's disclosure, adjustable depth controller 162 or spacer 164 can be adjustable in any one or more of many conventional manners of adjustment, separately or in combination, and the adjustable components of system 500 shown in FIGS. 18-19 are but a few of many possibilities. For example, adjustable depth controller 162 can have a spacer of fixed dimension, and the distance between the spacer and the system body can be adjustable, such as by way of sliding, threaded, or otherwise moveable features. As will also be understood by one of skill in the art, although adjustable depth controller 162 is described herein with reference to system 500 for illustrative purposes, the characteristics and components of these elements apply equally to all other lancing systems described herein, separately or in combination, specifically including, without limitation, systems 100, 300 and 400 described with reference to FIGS. 1-10.

Other and further embodiments utilizing one or more aspects of the invention described above can be devised without departing from the spirit of Applicant's invention. Further, the various methods and embodiments of the lancing system can be included in combination with each other to produce variations of the disclosed methods and embodiments. For example, unless the context requires otherwise, all of the elements and methods described with reference to the embodiments of FIGS. 1-10 apply equally to the embodiments of FIGS. 11-19, and vice-versa. Discussion of singular elements can include plural elements and vice-versa. References to at least one item followed by a reference to the item may include one or more items. Also, various aspects of the embodiments could be used in conjunction with each other to accomplish the understood goals of the disclosure. Unless the context requires otherwise, the word "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The invention has been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicant, but rather, in conformity with the patent laws, Applicant intends to fully protect all such modifications and improvements that come within the scope or range of equivalent of the following claims.

What is claimed is:

1. A vacuum assisted lancing system for blood extraction, comprising:
   a tubular body having a central longitudinal axis, a lancing end and a free end; a lancing mechanism coupled with the body and including a lance coupler configured to removably couple with a lance;
   a vacuum mechanism coupled with the body and including a piston slideably coupled within the body so that a vacuum chamber is formed between the piston and the lancing end of the body;
   a release mechanism configured to selectively hold the vacuum mechanism in an energized state;
   an opening through a wall of the body between the piston and the lancing end of the body that allows fluid communication back and forth between the vacuum chamber and an atmosphere surrounding the body; and
   at least one spring configured to
      simultaneously move both the lance coupler and the piston in an initial direction toward the free end of the body upon the release mechanism being activated to release the vacuum mechanism from the energized state and create a vacuum in the vacuum chamber, and thereafter move the lance coupler in a second direction toward the lancing end of the body.

2. The lancing system of claim 1, wherein the opening is configured to be sealingly engaged by a user so that the user can selectively block and unblock the opening.

3. The lancing system of claim 1, wherein the release mechanism further comprises a release, and wherein the opening is disposed in the release.

4. The lancing system of claim 3, wherein the release has an activated position, and wherein the opening is configured to be at least partially blocked when the release is in the activated position.

5. The lancing system of claim 1, further comprising a valve coupled to the opening.

6. The lancing system of claim 1, further comprising a depth controller having one end removably coupled to the lancing end of the body and a longitudinally opposite end configured to sealingly engage a surface to be lanced.

7. The lancing system of claim 6, wherein the depth controller is adjustable.

8. The lancing system of claim 6, wherein the depth controller further comprises a spacer having a variable thickness.

9. The lancing system of claim 1, further comprising a lance coupled to the lancing mechanism.

10. A vacuum assisted lancing system for blood extraction, comprising:
    a body having a first end adapted to sealingly engage a surface to be lanced, a longitudinally opposite second end, a vacuum chamber between the first and second ends, an opening through a wall of the body that allows fluid communication back and forth between the vacuum chamber and an atmosphere surrounding the vacuum chamber, and a lance coupler slideably disposed within the vacuum chamber;

means for selectively holding the lance coupler in a cocked position and releasing the lance coupler from the cocked position;

means for creating a vacuum in the vacuum chamber and acting on the surface to be lanced;

means for moving a lance initially in a first direction toward the second end of the body upon release of the lance coupler from the cocked position, stopping the lance, moving the lance in a longitudinally opposite second direction toward the surface to be lanced, and thereafter disposing the lance in contact with the surface while the vacuum is acting on the surface; and means for selectively commencing dissipation of the vacuum after the vacuum has acted on the surface for a period of time.

11. The lancing system of claim 10, wherein the opening through the body is disposed through a release.

12. The lancing system of claim 10, further comprising means for simultaneously initiating creation of the vacuum and at least partially blocking the opening through the body.

13. The lancing system of claim 10, further comprising means for dissipating the vacuum at a controlled rate.

14. The lancing system of claim 10, further comprising a lance coupled to the means for disposing a lance in contact with the surface.

15. A method of manipulating a surface for blood extraction with a vacuum assisted lancing system including a tubular body having a lancing end and a free end, a lancing mechanism coupled with the body and having a lance coupler configured to removably couple with a lance, a vacuum mechanism including a piston slideably coupled within the body so that a vacuum chamber is formed between the piston and the lancing end of the body, a release mechanism configured to selectively hold the vacuum mechanism in an energized state, and an opening through a wall of the body between the piston and the lancing end of the body that allows fluid communication back and forth between the vacuum chamber and an atmosphere surrounding the vacuum chamber, the method comprising:

coupling the lancing system to the surface;

blocking the opening;

activating the lancing system by actuating the release mechanism, thereby
creating a vacuum and subjecting the surface to the vacuum, and
simultaneously moving both the lance coupler and the piston in an initial direction toward the free end of the body until the lance coupler reaches a first position distal from the surface and thereafter moving the lance coupler from the first position distal from the surface to a second position proximal to the surface;
maintaining the vacuum for a period of time; and commencing dissipation of the vacuum by unblocking the opening, thereby allowing the surface to fluidicly communicate with an atmosphere surrounding the lancing system while the lancing system is coupled to the surface.

16. The method of claim 15, wherein the lancing system includes a release coupled with the opening, and wherein the blocking and activating steps are accomplished simultaneously by engaging and holding the release.

17. The method of claim 16, wherein commencing dissipation of the vacuum further comprises disengaging the release.

18. The method of claim 15, wherein blocking the opening further comprises sealingly engaging the opening with a finger, and wherein unblocking the opening further comprises disengaging the opening and the finger.

19. The method of claim 15, wherein the lancing system includes a lance removably coupled to the lance coupler, and wherein the method further comprises lancing the surface.

20. The method of claim 19, further comprising maintaining the vacuum for a period of time after the surface has been lanced.

* * * * *